US007687603B2

(12) United States Patent
Zhao et al.

(10) Patent No.: US 7,687,603 B2
(45) Date of Patent: Mar. 30, 2010

(54) GUANIDINIUM DELIVERY CARRIERS

(75) Inventors: Gang Zhao, Vista, CA (US); Lei Yu, Carlsbad, CA (US); Jian Liu, San Diego, CA (US); Chieko Kitaura, Osaka (JP); Xinghe Wang, San Diego, CA (US); Chris Castello, Vista, CA (US)

(73) Assignee: Nitto Denko Corporation, Osaka (JP)

( * ) Notice: Subject to any disclaimer, the term of this patent is extended or adjusted under 35 U.S.C. 154(b) by 463 days.

(21) Appl. No.: 11/526,224

(22) Filed: Sep. 22, 2006

(65) Prior Publication Data

US 2007/0078094 A1  Apr. 5, 2007

Related U.S. Application Data

(60) Provisional application No. 60/720,299, filed on Sep. 23, 2005.

(51) Int. Cl.
*A61K 38/05* (2006.01)
(52) U.S. Cl. .......................... 530/300; 530/331; 514/18
(58) Field of Classification Search ........................ None
See application file for complete search history.

(56) References Cited

U.S. PATENT DOCUMENTS

| | | | |
|---|---|---|---|
| 5,637,623 | A | 6/1997 | Goldin et al. |
| 6,235,711 | B1 | 5/2001 | Dutta |
| 2002/0107196 | A1 | 8/2002 | Gupta |
| 2002/0131965 | A1 | 9/2002 | Rothbard et al. |
| 2003/0073807 | A1 | 4/2003 | Wender et al. |
| 2005/0119167 | A1 | 6/2005 | Abbenante et al. |
| 2007/0104645 | A1 | 5/2007 | Garlich et al. |
| 2008/0221020 | A1 | 9/2008 | Goodman et al. |

FOREIGN PATENT DOCUMENTS

| | | | |
|---|---|---|---|
| WO | WO 02065986 | | 8/2002 |
| WO | WO 02069930 | | 9/2002 |
| WO | WO 03/049772 | * | 6/2003 |
| WO | WO 03049772 | | 6/2003 |
| WO | WO 2005/025513 | * | 3/2005 |
| WO | WO 2005/035549 | | 4/2005 |
| WO | WO 2006/044063 | | 4/2006 |

OTHER PUBLICATIONS

Diaz-Mochon et al., "Synthesis and cellular uptake of cell delivering PNA-peptide conjugates", *Chem. Commun.*, 2005, 3316-3318.
Dragulescu-Andrasi et al., "Cell-permeable GPNA with appropriate backbone stereochemistry and spacing binds sequence-specifically to RNA", *Chem. Commun.*, 2005, 2, 244-246.
Takahashi et al., "Design of a nucleobase conjugated peptide that recognizes HIV-1 RRE IIB RNA with high affinity and specificity", *Chem. Commun.*, 2002, 6:5, 349-350.
Zhou et al., "Novel Binding and Efficient Cellular Uptake of Guanidine-Based Peptide Nucleic Acids (GNPA)", *J. Am. Chem. Soc.*, 2003, 125:23, 6878-6879.

International Search Report for PCT/US2006/036743 dated Jul. 19, 2007.
Written Opinion for PCT/2006/036743 dated Jul. 19, 2007.
International Search Report for PCT/US2006/036745 dated Aug. 16, 2007.
Written Opinion for PCT/US2006/036745 dated Aug. 16, 2007.
Futaki et al., "Translocation of Branched-Chain Arginine Peptides through Cell Membranes: Flexibility in the Spatial Disposition of Positive Charges in Membrane-Permeable Peptides", *Biochemistry*, 2002, 41, 7925-7930.
Futaki, "Membrane-permeable arginine-rich peptides and the translocation mechanisms", *Advanced Drug Delivery Reviews 57*, 2005, 547-558.
Wright et al., "Guanidinium Rich Peptide Transporters and Drug Delivery", *Current Protein and Peptide Science*, 2003, 4, 105-124.
International Search Report for PCT/US2006/036746 dated May 14, 2007.
Written Opinion for PCT/US2006/036746 dated May 14, 2007.
Klein, "Hydrogen isotope effects in the reactions catalyzed by $H_2$-forming $N^5,N^{10}$-methylenetrahydromethanopterin dehydrogenase from methanogenic Archaea," *Eur. J. Biochem.*, Oct. 1, 1995;233(1):372-376.
Office Action dated Oct. 17, 2008 in U.S. Appl. No. 11/525,482, filed Sep. 21, 2006.
Alm et al., "Effects of topically applied PGF2 alpha and its isopropylester on normal and glaucomatous human eyes", *Prog. Clin. Biol. Res.*, 1989, 312, 447-458.
Fuchs et al., "Pathway for Polyarginine Entry into Mammalian Cells Biochemistry", 2004, 43, 2438-2444.
Jiang et al., "Tumor imaging by means of proteolytic activation of cell-penetrating peptides", *Proceedings of the National Academy of Sciences of USA*, 2004, 101, 17867-17872.
Joshi, "Microparticulates for ophthalmic drug delivery", *J. Ocul. Pharmacol.*, 1994, 10, 29-45.
Kirschberg et al., "Arginine-based molecular transporters: the synthesis and chemical evaluation of releasable taxol-transporter conjugates", *Organic Letters*, 2003, 5, 3459-3462.
Lagerholm et al., "Multicolor coding of cells with cationic peptide coated quantum dots", *Nano Letters American Chem. Soc. USA*, 2004, 4, 2019-2022.
Maiolo et al., "Effects of cargo molecules on the cellular uptake of arginine-rich cell-penetrating peptides", *Biochim. Biophys. Acta*, 2005, 1712, 161-172.
Mayer et al., "Efficacy of a novel hydrogel formulation in human volunteers", *Ophthalmologica*, 1996, 210, 101-103.

(Continued)

*Primary Examiner*—Christopher R. Tate
*Assistant Examiner*—Roy Teller
(74) *Attorney, Agent, or Firm*—Knobbe, Martens, Olson & Bear LLP

(57) ABSTRACT

Disclosed herein are transmembrane transporter compounds containing guanidinium groups. Also disclosed herein are methods for transporting a biologically active moiety across a biological membrane using the transmembrane transporter compounds. Particularly, this invention provides a method for the delivery of a biologically active moiety across the biological membranes of such membranes as endothelial tissues.

7 Claims, 14 Drawing Sheets

OTHER PUBLICATIONS

Mordenti et al., "Intraocular pharmacokinetics and safety of a humanized monoclonal antibody in rabbits after intravitreal administration of a solution or a PLGA microsphere formulation", *Toxicol. Sci.*, 1999, 52, 101-106.

Rothbard et al., "Arginine-rich molecular transporters for drug delivery; role of backbone spacing in cellular uptake", *J. Medicinal Chem.*, 2002, 45, 3612-3618.

Shedden et al., "Efficacy and tolerability of timolol maleate ophthalmic gel-forming solution versus timolol ophthalmic solution in adults with open-angle glaucoma or ocular hypertension: a six-month, double-masked, multicenter study", *Clin. Ther.*, 2001, 23, 440-450.

Thomson et al., "Fmoc mediated synthesis of Peptide Nucleic Acids", *Tetrahedron*, 1995, 51(22), 6179-6194.

International Search Report for PCT/US2006/036746 dated Mar. 1, 2007.

Edwards et al., "Evaluation of radiolabeled type IV collagen fragments as potential tumor imaging agents," *Bioconj. Chem.* 2001, 12(6):1057-1065.

Tamamura et al., "Identification of novel low molecular weight CXCR4 antagonists by structural tuning of cyclic tetrapeptide scaffolds," *J. Med. Chem.* 2005, 48(9):3280-3289.

Office Action dated Jun. 11, 2009 for U.S. Appl. No. 11/525,482, filed Sep. 21, 2006.

Office Action dated Mar. 19, 2009 for U.S. Appl. No. 11/525,482, filed Sep. 21, 2006.

Office Action dated Jul. 1, 2009 for U.S. Appl. No. 11/525,512, filed Sep. 21, 2006.

\* cited by examiner

GUANIDINIUM DELIVERY CARRIERS

This application claims priority to U.S. Provisional Application No. 60/720,299, entitled "BRANCHED AND SYMMETRIC GUANIDINIUM COMPOUNDS", filed Sep. 23, 2005, which is incorporated by reference in its entirety.

BACKGROUND OF THE INVENTION

1. Field of the Invention

The present invention relates to the fields of chemistry and medicine. More particularly, the present invention relates to guanidinium containing compounds that exhibit enhanced transmembrane transport of biologically active molecules.

2. Description of the Related Art

Protein transduction domains (PTD) are short cationic peptides that are capable of delivering molecules into mammalian cells. They include many diverse peptide sequences from many diverse sources. The phenomenon that peptide sequences can assist molecules across biological barriers is ubiquitous in biological systems. Such phenomenon can take place at different levels, including subcellular (e.g., nuclear membranes), cellular (e.g., cell membranes), and tissue levels (e.g., epithelial tissue). Sometimes the same peptide sequences can promote different translocation events at different biological levels.

SUMMARY OF THE INVENTION

Disclosed herein are compounds and methods for transporting a biologically active moiety across a biological membrane. In some embodiments, the rate of transport across the membrane of the biologically active moiety is greater for the conjugated form compared to the non-conjugated form.

One embodiment disclosed herein includes a compound of Formula (I):

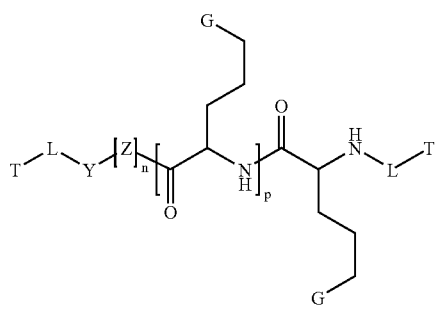

(I)

wherein each T is a terminal group independently selected from the group consisting of hydrogen, an alkylcarbonyl, an amine, a carboxylic group, a N-terminal peptide, a group that forms an N-terminal peptide bond, a C-terminal peptide, a group that forms a C-terminal peptide bond, a reporting moiety, an imaging agent moiety, and a therapeutic moiety;

wherein Z has the structure:

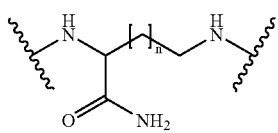

wherein s is 0 or 1;
wherein when s is 1, Y has the structure:

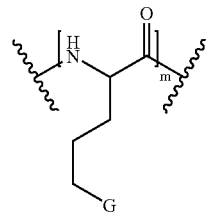

wherein when s is 0, Y has the structure:

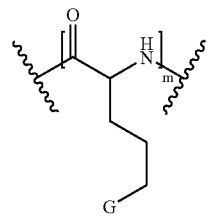

wherein m is an integer from 1 to 6;
wherein n is an integer from 0 to 10;
wherein p is an integer from 0 to 5;
wherein the sum of m and p is an integer from 6 to 11;
wherein each G is separately selected to be a guanidinium group having the formula:

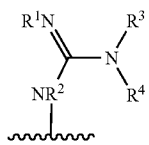

wherein the point of attachment of G is through a nitrogen atom or through $R^2$ or each G is separately selected from the group consisting of:

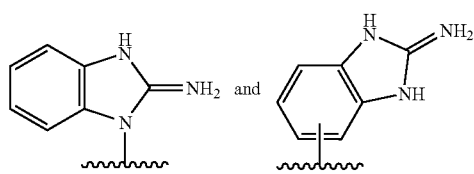

wherein:

each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;

each $R^1$ is optionally bound to the $R^2$, $R^3$, or $R^4$ on the same guanidinium group to form a heterocyclic ring;

each $R^2$ is optionally bound to the $R^3$ or $R^4$ on the same guanidinium group to form a heterocyclic ring; and each $R^3$ is optionally bound to the $R^4$ on the same guanidinium group to form a heterocyclic ring; and wherein each L is a linker moiety independently selected from the group consisting of mono-substituted, poly-substituted or unsubstituted variants of the following residues: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group, or L is absent.

In some embodiments, each G is separately selected from the group consisting of:

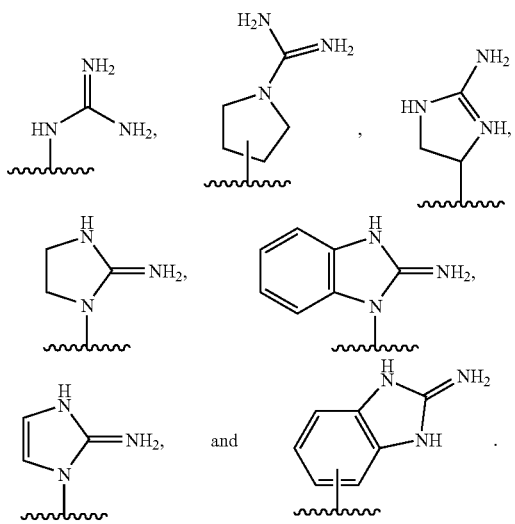

In some embodiments, $R^1$, $R^2$, $R^3$, and $R^4$ are hydrogen.

In other embodiments, at least one T can be a reporting moiety, an imaging agent moiety, or a therapeutic moiety. In some embodiments, at least one T can be a peptide nucleic acid. In other embodiments, at least one T can have the formula:

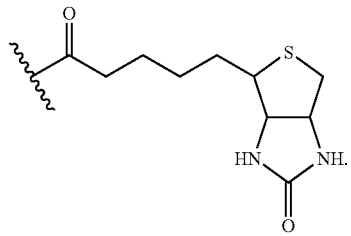

In yet still other embodiments, at least one T can have the formula:

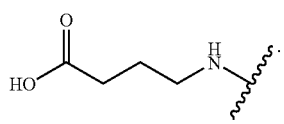

In some embodiments, at least one T can be a polypeptide. In other embodiments, at least one T can be a protein antigen. In still other embodiments, at least one T can be a tumor antigen. In yet still embodiments, at least one T can be a tisane moiety. In some embodiments, at least one T can be a metal ion. In other embodiments, at least one T can be an antimicrobial agent. In yet still other embodiments, at least one T can be an epitope tag (e.g., CYPYDVPDYA). In some embodiments, the therapeutic moiety can be an anti-cancer agent. Specifically, in another embodiment, the anti-cancer agent may be an anti-tumor agent. More specifically, in still another embodiment, the anti-tumor agent can be doxorubicin or a platinum metal complex. An exemplary platinum metal complex is the following:

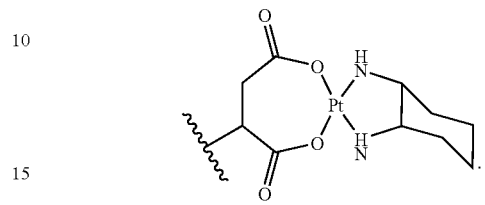

In some embodiments, at least one T can be an imaging agent moiety. In certain embodiments, the imaging agent moiety can be a gadolinium metal complex. An exemplary gadolinium metal complex is the following:

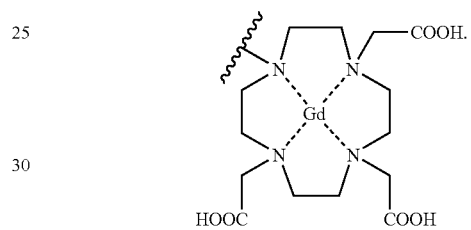

With respect to the linker moiety (L), in one embodiment, each L may be independently selected from the group consisting of mono-substituted, poly-substituted or unsubstituted variants of the following residues: $C_1$-$C_{12}$ alkyl, $C_2$-$C_{12}$ alkenyl, $C_2$-$C_{12}$ alkynyl, $C_1$-$C_{12}$ heteroalkyl, $C_2$-$C_{12}$ heteroalkenyl, $C_2$-$C_{12}$ heteroalkynyl, amide, ester, and disulfide group. In another embodiment, each L may be independently selected from the group consisting of mono-substituted, poly-substituted or unsubstituted variants of the following residues: $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, amide, ester, and disulfide group. In still another embodiment, each L may be independently selected from the group consisting of: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group optionally substituted with substituents selected from the group consisting of halogen, acyl, alkoxy, cycloalkoxy, aryl, heteroaryl, arylalkoxy carbonyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl. In some embodiments, the linker can have a first cleavable group and a second cleavable group, wherein when the first cleavable group is cleaved, the first cleavable group is converted to a nucleophilic moiety that is adapted to react with the second cleavable group. In some embodiments, the first group can be an amide group and the second group can be an ester group, and cleavage of the amide group yields a free amino group that reacts with the ester group. In some embodiments, the first group can be a phosphate ester group and the second group can be a carboxylate ester group, and cleavage of the phosphate ester group yields a free hydroxyl group that reacts with the carboxylate ester group.

In one embodiment, a compound of Formula (I) can have the following structure:
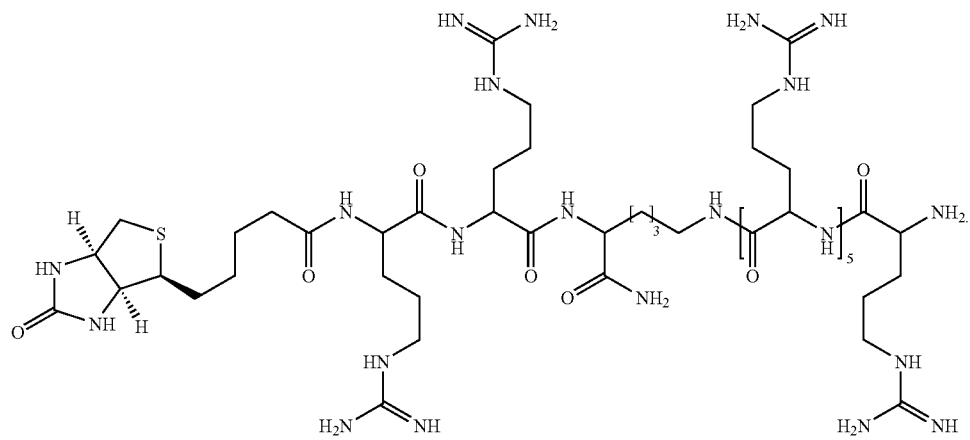
In another embodiment, a compound of Formula (I) can have the following structure:
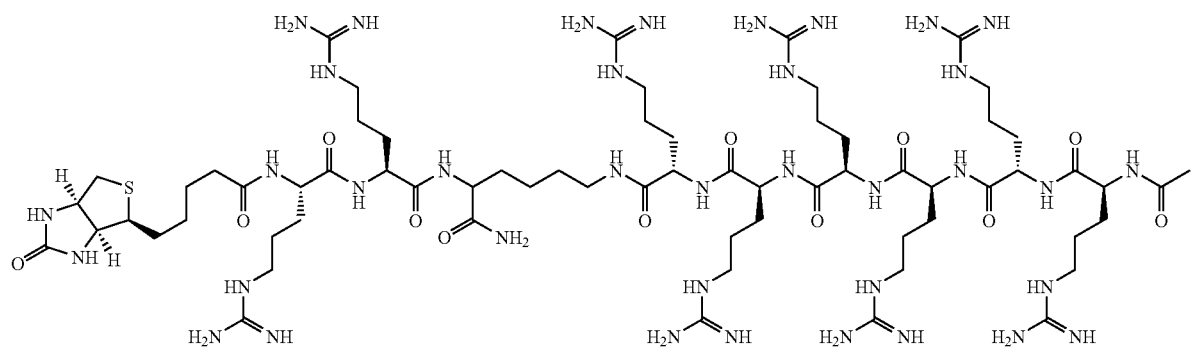
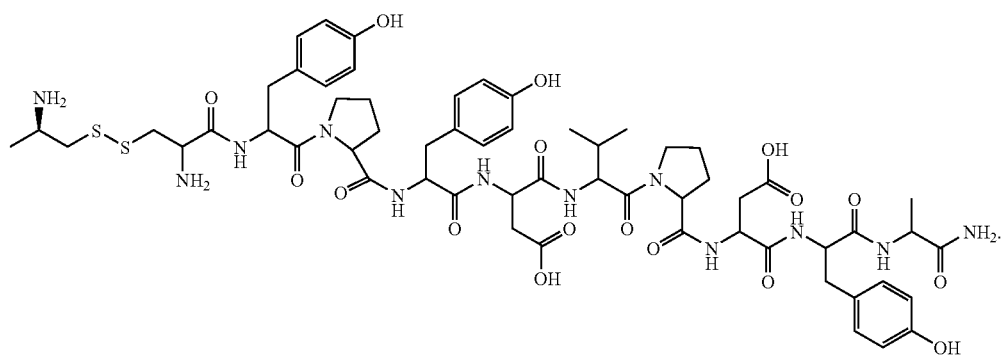

In still another embodiment, a compound of Formula (I) can have the following structure:

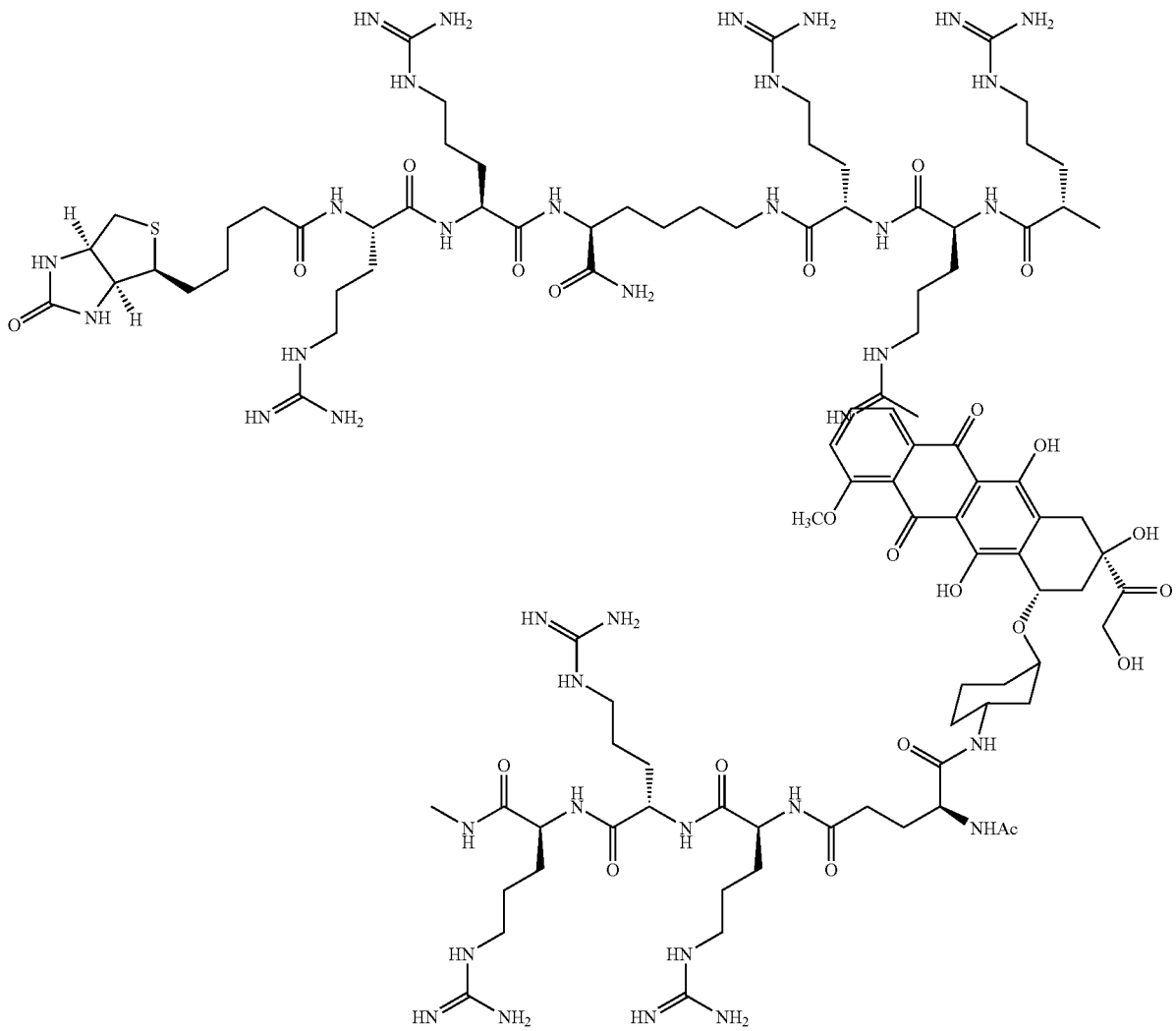

Another embodiment disclosed herein includes a compound of Formula (II):

(II)

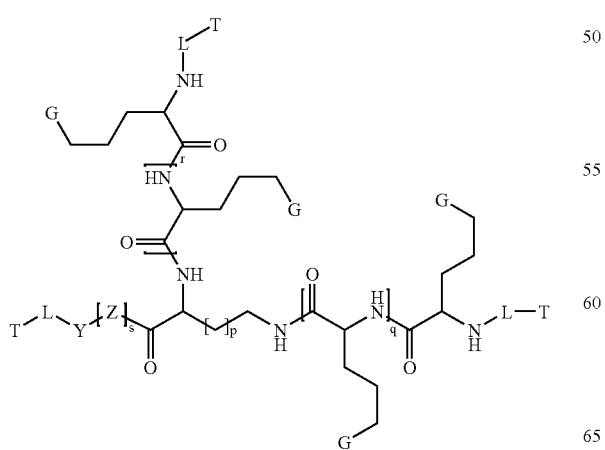

wherein each T is a terminal group independently selected from the group consisting of hydrogen, an alkylcarbonyl, an amine, a carboxylic group, a N-terminal peptide or group that forms an N-terminal peptide bond, a C-terminal peptide or group that forms a C-terminal peptide bond, a reporting moiety, an imaging agent moiety, and a therapeutic moiety;

wherein Z has the structure:

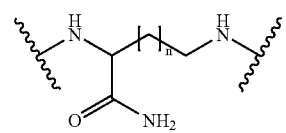

wherein s is 0 or 1;
wherein when s is 1, Y has the structure:

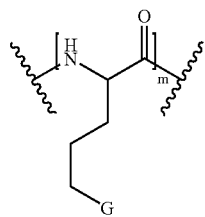

wherein when s is 0, Y has the structure:

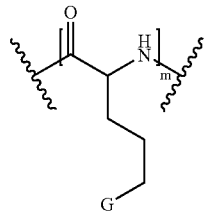

wherein p is an integer from 0 to 10;
wherein q is an integer from 0 to 5;
wherein r is an integer from 0 to 5;
wherein m is an integer from 1 to 6;
wherein n is an integer from 0 to 10;
wherein the sum of m, q, and r is an integer from 6 to 16;
wherein each G is separately selected to be a guanidinium group having the formula:

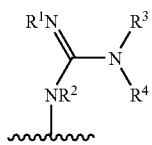

wherein the point of attachment of G is through a nitrogen atom or through $R^2$ or each G is separately selected from the group consisting of:

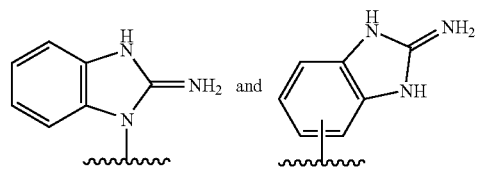

wherein:
each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;
each $R^1$ is optionally bound to the $R^2$, $R^3$, or $R^4$ on the same guanidinium group to form a heterocyclic ring;
each $R^2$ is optionally bound to the $R^3$ or $R^4$ on the same guanidinium group to form a heterocyclic ring; and
each $R^3$ is optionally bound to the $R^4$ on the same guanidinium group to form a heterocyclic ring; and wherein each L is a linker moiety independently selected from the group consisting of mono-substituted, poly-substituted or unsubstituted variants of the following residues: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group, or L is absent.

In some embodiments, each G is separately selected from the group consisting of:

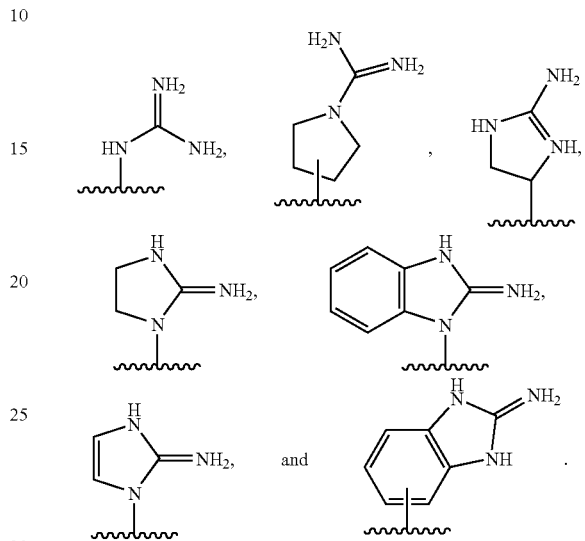

In some embodiments, $R^1$, $R^2$, $R^3$, and $R^4$ are hydrogen.
In other embodiments, at least one T can be a reporting moiety, an imaging agent moiety, or a therapeutic moiety. In some embodiments, at least one T can be a peptide nucleic acid. In other embodiments, at least one T can have the formula:

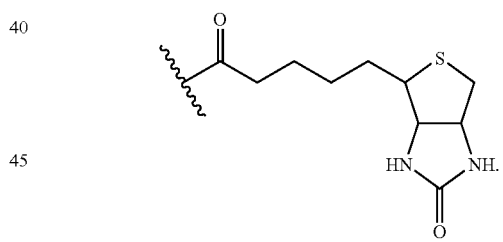

In yet still other embodiments, at least one T can have the formula:

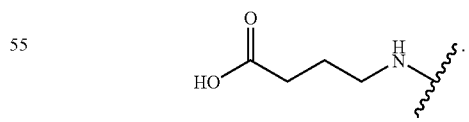

In some embodiments, at least one T can be a polypeptide. In other embodiments, at least one T can be a protein antigen. In still other embodiments, at least one T can be a tumor antigen. In yet still embodiments, at least one T can be a tisane moiety. In some embodiments, at least one T can be a metal ion. In other embodiments, at least one T can be an antimicrobial agent. In yet still other embodiments, at least one T can be an epitope tag (e.g., CYPYDVPDYA). In some embodiments, the therapeutic moiety can be an anti-cancer agent. Specifically, in another embodiment, the anti-cancer agent may be an anti-tumor agent. More specifically, in still another embodiment, the anti-tumor agent can be doxorubicin or a platinum metal complex. An exemplary platinum metal complex is the following:

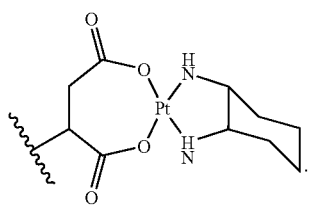

In some embodiments, at least one T can be an imaging agent moiety. In certain embodiments, the imaging agent moiety can be a gadolinium metal complex. An exemplary gadolinium metal complex is the following:

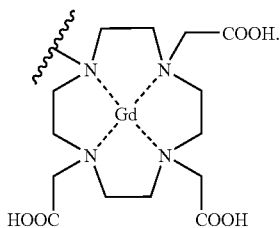

Referring to the linker moiety (L), in one embodiment, each L may be independently selected from the group consisting of mono-substituted, poly-substituted or unsubstituted variants of the following residues: $C_1$-$C_{12}$ alkyl, $C_2$-$C_{12}$ alkenyl, $C_2$-$C_{12}$ alkynyl, $C_1$-$C_{12}$ heteroalkyl, $C_2$-$C_{12}$ heteroalkenyl, $C_2$-$C_{12}$ heteroalkynyl, amide, ester, and disulfide group. In another embodiment, each L may be independently selected from the group consisting of mono-substituted, poly-substituted or unsubstituted variants of the following residues: $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, amide, ester, and disulfide group. In still another embodiment, each L may be independently selected from the group consisting of: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group optionally substituted with substituents selected from the group consisting of halogen, acyl, alkoxy, cycloalkoxy, aryl, heteroaryl, arylalkoxy carbonyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl. In some embodiments, the linker can have a first cleavable group and a second cleavable group, wherein when the first cleavable group is cleaved, the first cleavable group is converted to a nucleophilic moiety that is adapted to react with the second cleavable group. In some embodiments, the first group can be an amide group and the second group can be an ester group, and cleavage of the amide group yields a free amino group that reacts with the ester group. In some embodiments, the first group can be a phosphate ester group and the second group can be a carboxylate ester group, and cleavage of the phosphate ester group yields a free hydroxyl group that reacts with the carboxylate ester group.

In one embodiment, the compound of Formula (II) can have the following structure:

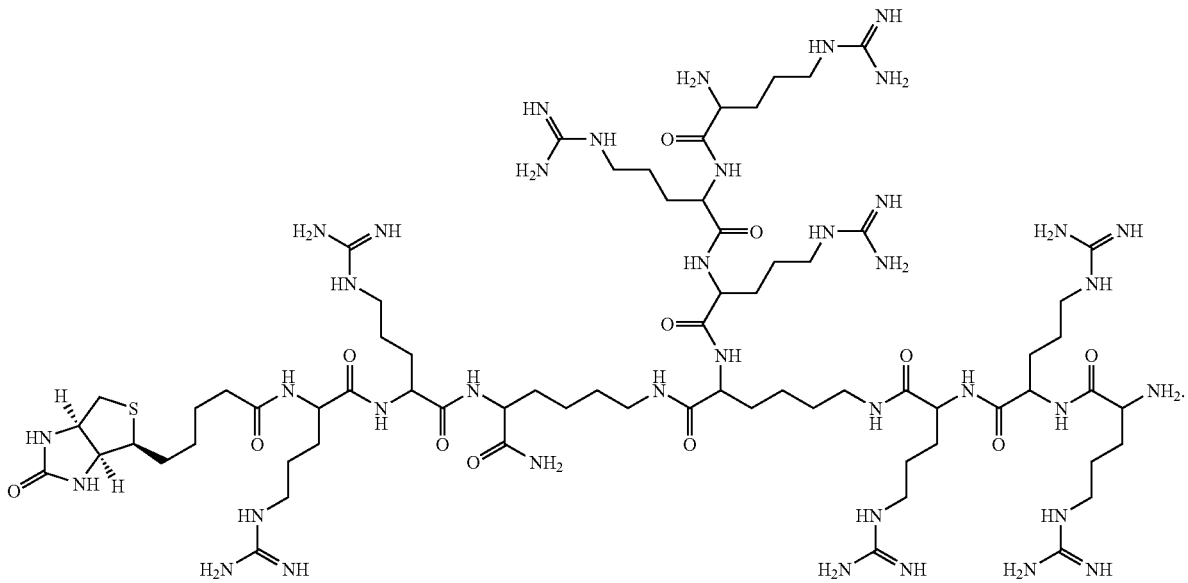

In another embodiment, the compound of Formula (II) can have the following structure:
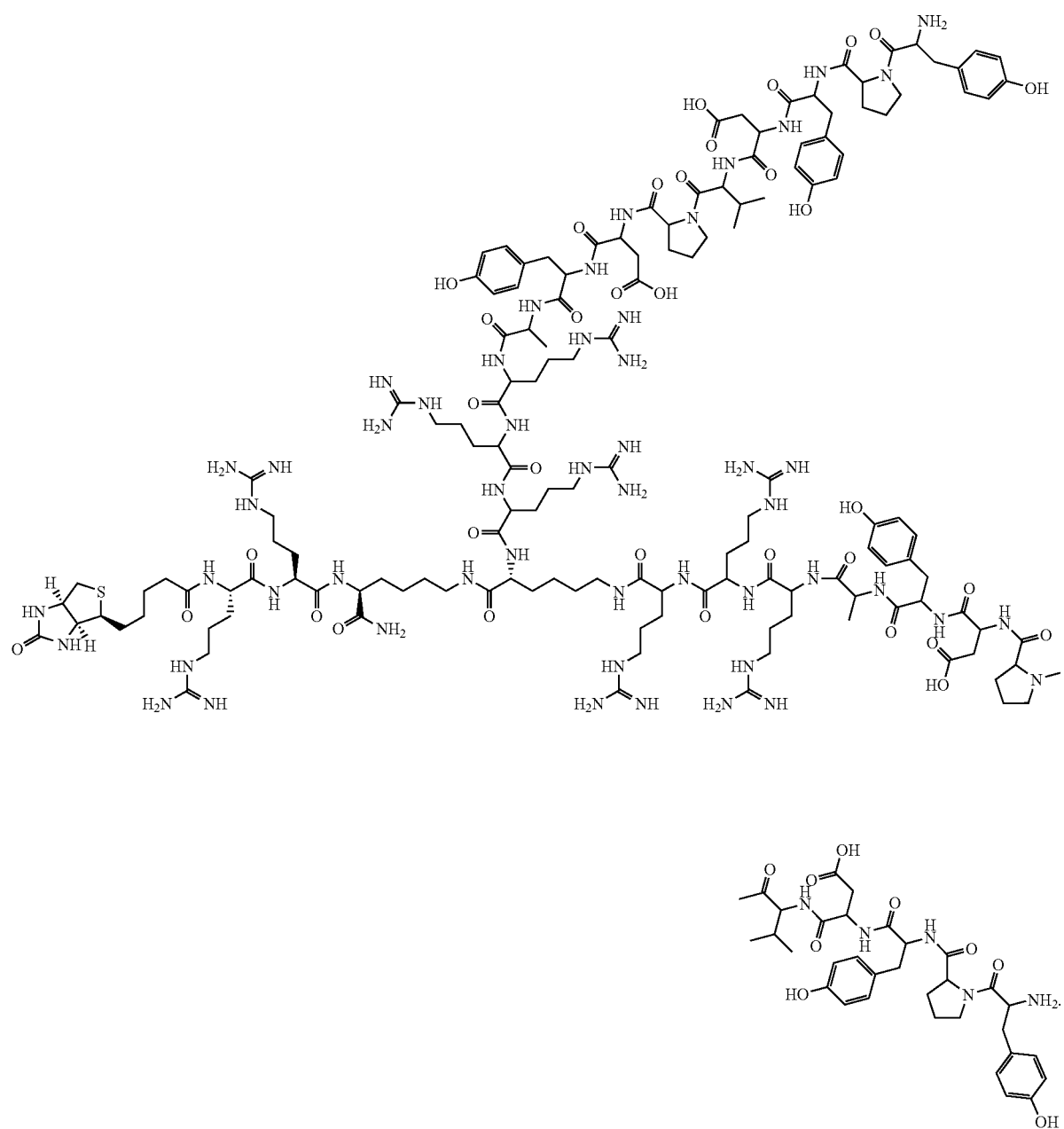

In yet another embodiment, the compound of Formula (II) can have the following structure:
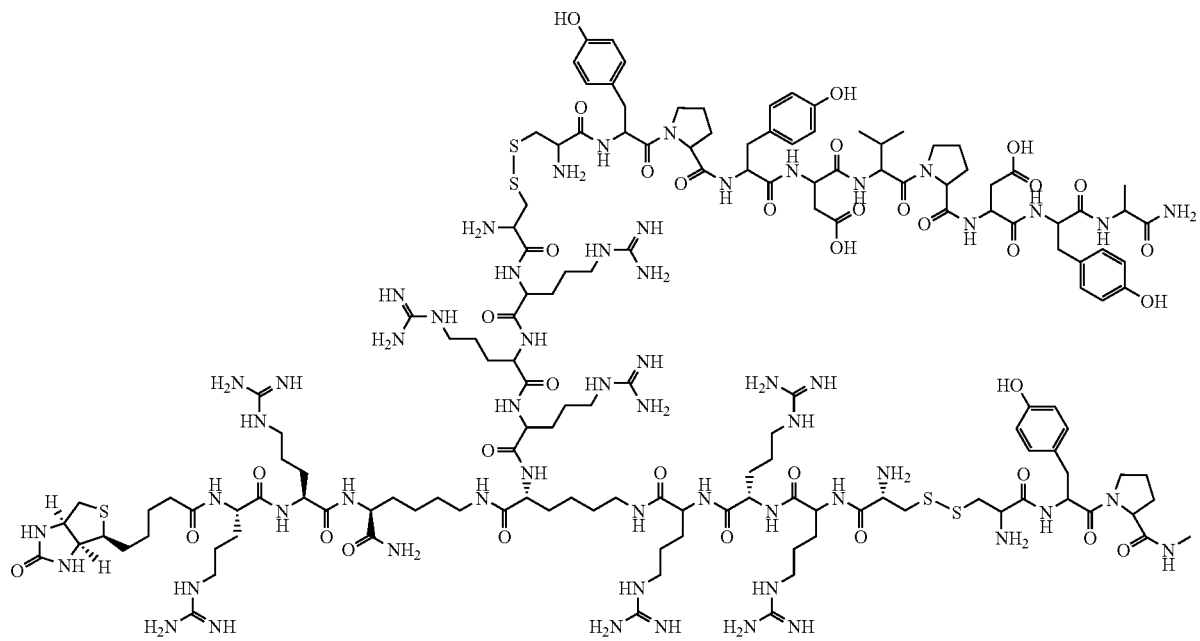
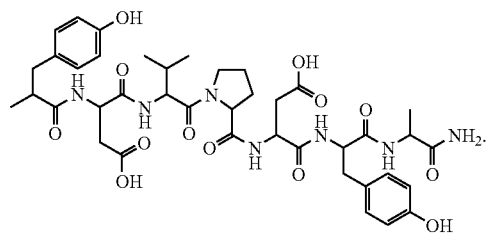
In another embodiment, the compound of Formula (II) can have the following structure:
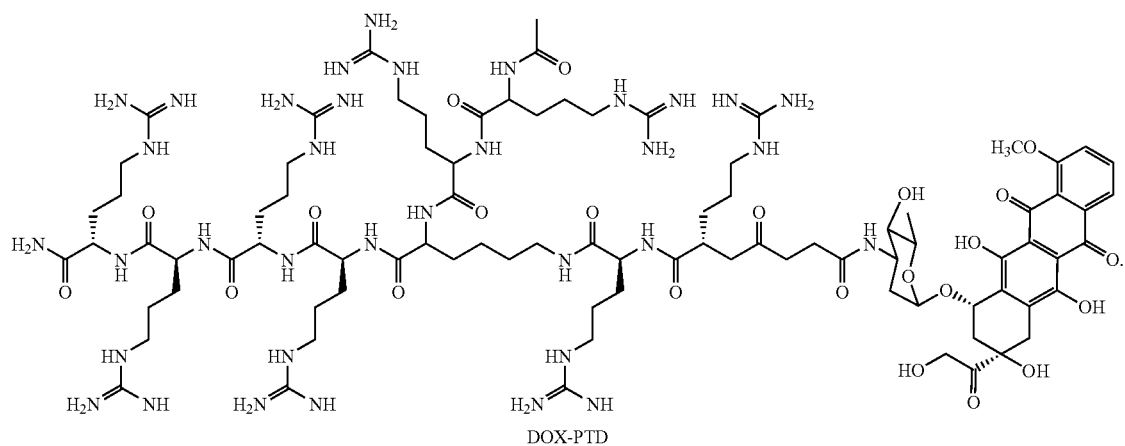
DOX-PTD In another embodiment, the compound of Formula (II) can have the following structure:

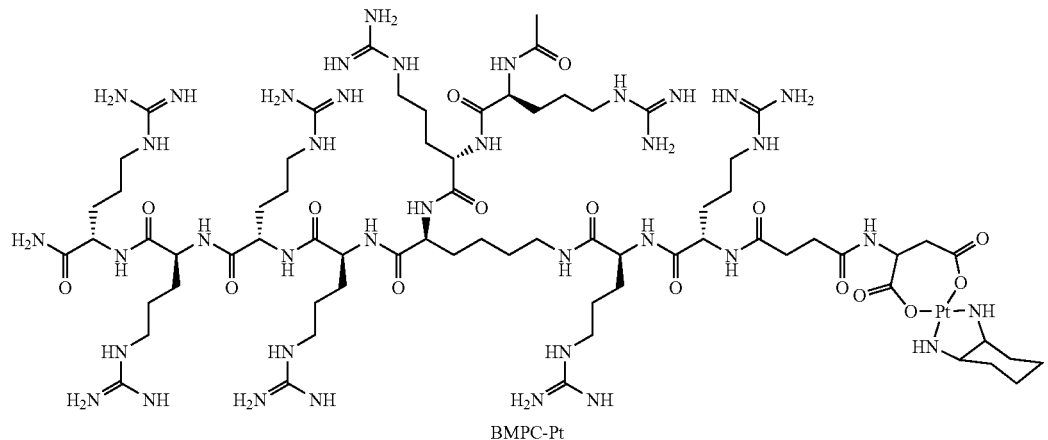

BMPC-Pt

In still another embodiment, the compound of Formula (II) can have the following structure:

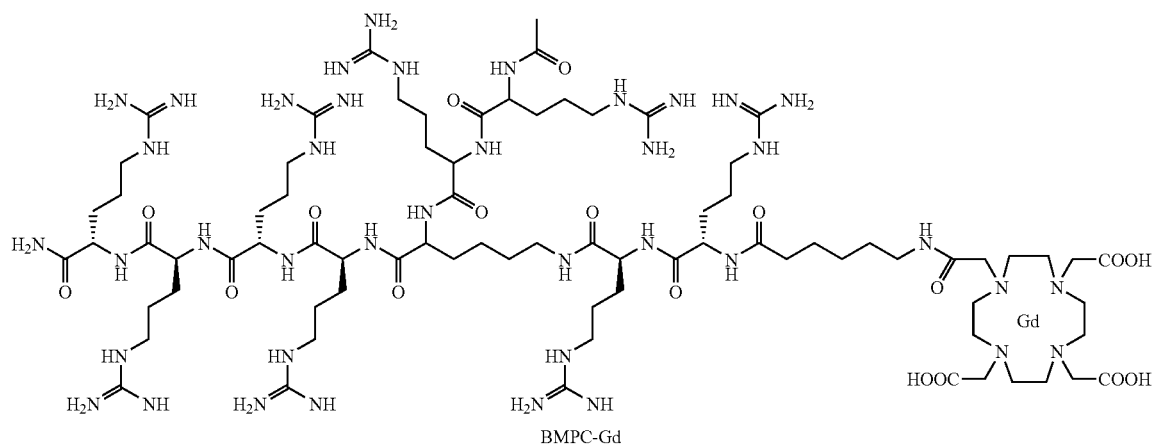

BMPC-Gd

One embodiment disclosed herein includes a method for transporting a biologically active moiety across a biological membrane, comprising contacting a biological membrane with a compound of Formula (I) or (II), or a pharmaceutically acceptable salt and pro-drug ester thereof. In some embodiments, the contacting can be effective in promoting the transport of the biologically active moiety (e.g., reporting moiety, the imaging agent moiety, or therapeutic moiety) across the biological membrane at a rate that is greater than a trans-membrane transport rate of the biologically active moiety in non-conjugated form.

In some embodiments, the biological membrane can be an eukaryotic cell membrane. The eukaryotic cell may be selected from the group consisting of a mammalian cell, a cancer cell, an insect cell, a plant cell, and a yeast cell. If the eukaryotic cell is a cancer cell, the cancer cell may be a prostate or melanoma cancer cell. In other embodiments, the biological membrane is an epithelial layer in a body. The epithelial layer can be skin, mucosmembrane or brain blood barrier. In still other embodiments, the biological membrane can be a prokaryotic cell membrane, such as a bacterial cell membrane.

Another embodiment disclosed herein describes a method of treating cancer comprising contacting a cancer cell in a subject with a compound having the structure of Formula (I) or (II), or a pharmaceutically acceptable salt and pro-drug ester thereof. In some embodiments, the contacting can be effective in promoting the transport of the therapeutic moiety across the biological membrane of the cancer cell at a rate that is greater than a trans-membrane transport rate of the therapeutic moiety in non-conjugated form.

In one embodiment, the cancer cell can be a prostate cancer cell. In another embodiment, the cancer cell can be a melanoma cancer cell.

The subject, in some embodiments, can be a mammal. In other embodiments, the subject can be a rodent. While in still other embodiments, the subject may be a human.

Some of the embodiments disclosed herein may further comprise identifying a subject in need of a therapeutic agent.

DETAILED DESCRIPTION OF THE PREFERRED EMBODIMENT

Figure 1A:
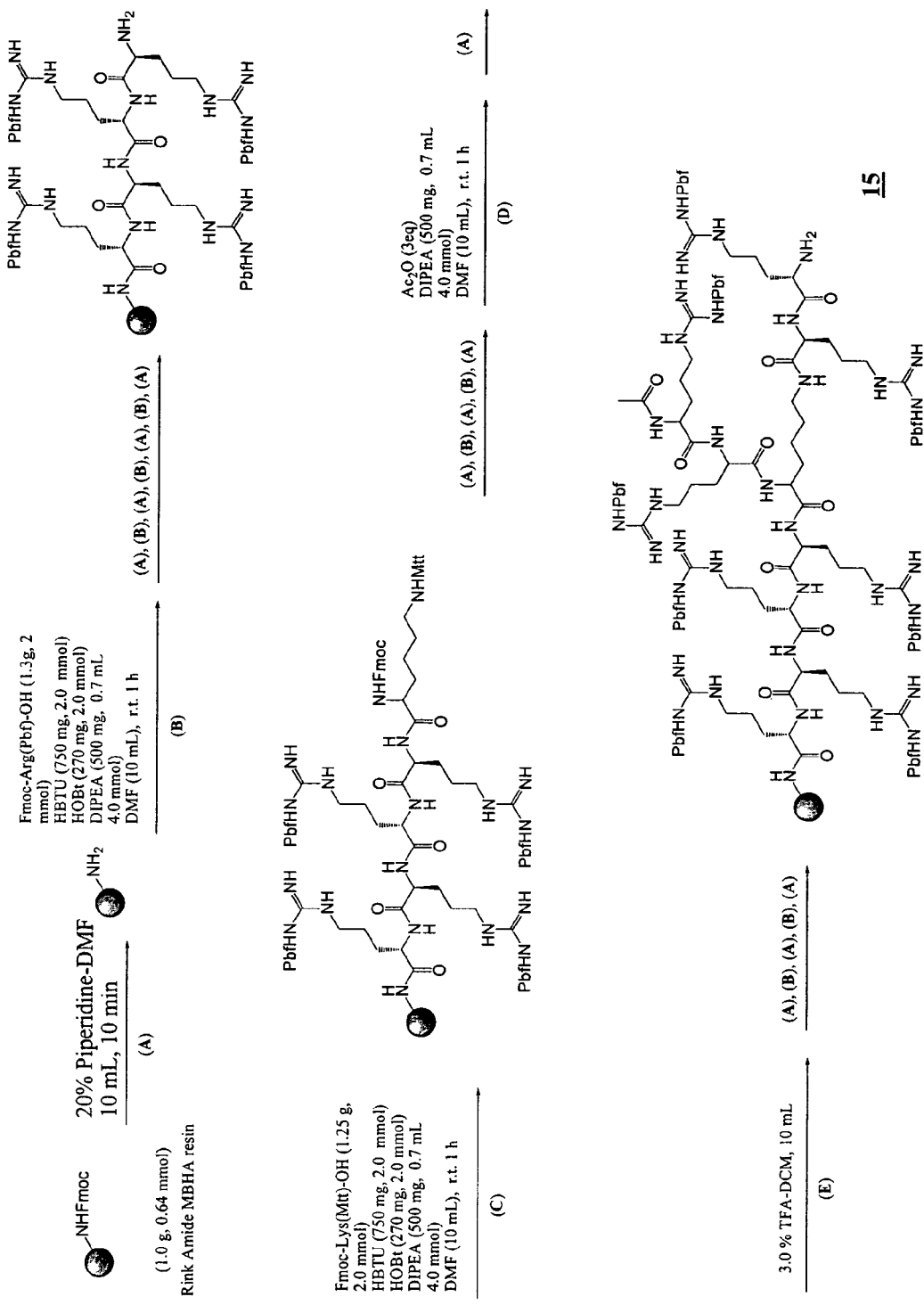
FIGS. 1A and 1B show a method for synthesizing doxorubicin-protein transduction domain (DOX-PTD).
Figure 1B:
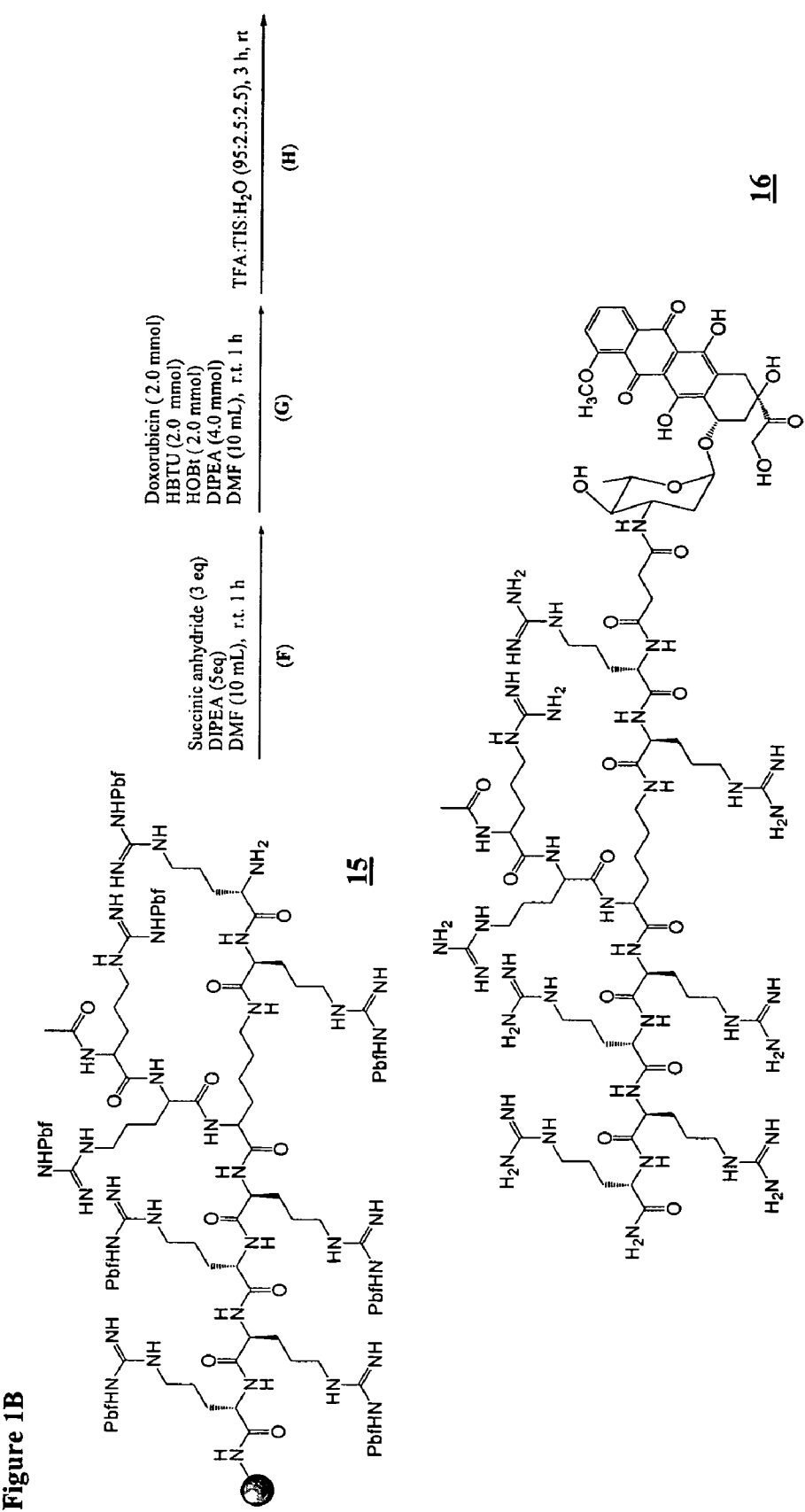

Branched-chain polymers, such as dendrimers, can be used as a carrier for the delivery of DNA and pharmaceuticals to cells. Branched polypeptides presenting multiple antigen recognition sites have also been utilized for vaccination. Accordingly, benefits of branched molecules as carriers have been demonstrated. However, for such branched scaffolds to be effective, they need to be able to cross biological membranes such as cell membranes and epithelial tissues. Thus, there is need for branched-chain and other asymmetric molecular scaffolds that have the characteristic of easily crossing biological membranes.

In some embodiments, a guanidinium containing transporter molecule is provided having one or more therapeutic moieties attached thereto. Thus, the transporter-therapeutic complex can be readily transported into a cell where the therapeutic moiety can have therapeutic effect. Any therapeutic moiety that can be covalently bound to the transporter molecules disclosed herein may be used. Non-limiting examples of some therapeutic moieties include: immunosuppressives, antibacterials, antifungals, antivirals, antiproliferatives, hormones, antiinflammatories, vitamins, analgesics, diagnostics and imaging contrast agents. Some specific examples include: conjugated glucocorticoids for treating inflammatory skin diseases, conjugated retinoids for treating acne, skin cancer and psoriasis, conjugated cytotoxic and immunosuppressive drugs for treating cancer and leukemia, conjugated antiinflammatory and antifungal agents, conjugated antihistamines, conjugated anagelsics, conjugated photochemotherapeutic agents, sunscreen, conjugated antibiotics for treating bacteria infections, conjugated anti-neoplastic agents for treating cancers, conjugated antiinflammatory agents, bronchodialators and immunosuppressive drugs for treating pulmonary conditions, conjugated neurotransmitters, and analgesics and CNS drugs that are capable of crossing the blood brain barrier.

In some embodiments, the therapeutic moiety is attached to the transporter molecule via a linker moiety. The linker moiety may be such that once the transporter-therapeutic complex is transported into a cell, the linker is cleaved, freeing the therapeutic moiety from the complex. Those of skill in the art will recognize many linkers suitable for this purpose. Non-limiting examples of linkers include moieties containing disulfide functionalities or acid-degradable functionalities such as esters. In some embodiments, a targeting moiety may also be attached to the multivalent arginine transporter molecule. The targeting moiety may be any moiety that preferentially binds to receptors on one or more cell types. Thus, a transporter-targeting-therapeutic complex is provided that preferentially is transported into one or more cell types where the therapeutic moiety can have therapeutic effect. Those of skill in the art will recognize many suitable targeting moieties. Non-limiting examples of some targeting moieties include: small molecules, oligo peptides, oligonucleotides, and macromolecules obtainable from synthetic or natural resources that have specific interactions with molecular targets implicated in the following diseases, including Acute lymphoblastic leukemia, Advanced pancreatic tumor, Affective disorder, AIDS, Allergic rhinitis, Allergy, Alzheimer's, Analgesic, Anesthesia, ANF degradation, Angiogenesis, Anxiety, Arthritis, Asthma, Autoimmune disease, Bacterial infection, Baldness, Blood coagulation, Bone Loss, Brain ischaemia, Breast cancer, Calcium deficiency, Carcinoid syndrome, Cardiac failure, Cardiovascular disease, Chronic myelogenous leukemia, Cognitive dysfunction, Colon cancer, Common cold, Common roundworm, Congestive heart failure, Cystic fibrosis, Dementia, Depression, Diabetes, Diabetic retinopathy, Diarrhea, Drug dependence, Erectile dysfunction, Fever, Fungal infection, Gastric tumor, Glaucoma, Gout, Heart disease, Heart failure, Helminth infection, Hepatitis C, Herpes, High blood glucose level, High blood sugar level, High cholesterol, Hirsutism, Hormone-dependent tumors, Human African trypanosomiasis, Hypertension, Hyperthyroidism, Hypocalcaemia, Immune response, Immunodeficiency, Inflammation, Influenza A and B, Insomnia, Irritable bowel syndrome, Kidney failure, Leukemia, Liposarcoma, Liver, Local anesthetic, Lung cancer, Lupus, Malaria, Malignant pain, Melanoma, Metastasis, Migraine, Morning sickness, Motion sickness, Motor disorder, Movement disorder, Nasal congestion, Neurodegeneration, Neuropathic, Obesity, Obstructive pulmonary disease, Ocular hypertension/glaucoma, Osteoporosis, Ovarian, Pain, Parkinson's, Peptic ulcer, Phaeochromocytoma, Platelet adhesion, Platelet disease, Posterior pituitary disorder, Postsurgical pain, Prostate adenocarcinoma, Prostate tumor, Prostatic hyperplasia, Psychiatric illness, Psychomotor, Reproduction diseases, Respiration diseases, Rheumatoid, Riboflavin deficiency, Schizophrenia, Seizure, Smoking addiction, Solid tumor, Thiamine deficiency, Tuberculosis, Urinary tract infection, Urticaria, Uterus contraction, Vascular disease, Viral infection, Visceral, Vitamin A deficiency, Vitamin B12 deficiency, Vitamin B6 deficiency, Vitamin C deficiency, Vitamin D deficiency, Vomiting, and Zollinger-Ellison syndrome.

Definitions

As used herein, the term "alkyl" group refers to a saturated hydrocarbon group. An "alkenyl" group refers to a group consisting of at least two carbon atoms and at least one carbon-carbon double bond, and an "alkynyl" group refers to a group consisting of at least two carbon atoms and at least one carbon-carbon triple bond. The alkyl, alkene, and alkyne moieties may be branched, straight chain, or cyclic. Moreover, the alkyl, alkenyl and alkynyl groups may be substituted or unsubstituted.

The alkyl group may have 1 to 24 carbon atoms (whenever it appears herein, a numerical range such as "1 to 24" refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. The alkyl group may be substituted or unsubstituted.

The term "heteroalkyl" as used herein is a broad term and is used in its ordinary sense, including, without limitation, to refer to an alkyl having at least one heteroatom selected from nitrogen, oxygen, and sulfur, in the hydrocarbon chain.

The term "heteroalkenyl" as used herein is a broad term and is used in its ordinary sense, including, without limitation, to refer to an alkenyl having at least one heteroatom selected from nitrogen, oxygen, and sulfur, in the hydrocarbon chain.

The term "heteroalkynyl" as used herein is a broad term and is used in its ordinary sense, including, without limitation, to refer to an alkynyl having at least one heteroatom selected from nitrogen, oxygen, and sulfur, in the hydrocarbon chain.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group of this invention may be substituted or unsubstituted.

As used herein, "heteroaryl" refers to a monocyclic or multicyclic aromatic ring system (a ring system with fully delocalized pi-electron system), one or two or more fused rings that contain(s) one or more heteroatoms, that is, an element other than carbon, including but not limited to, nitrogen, oxygen and sulfur. The heteroaryl group may be optionally fused to a benzene ring. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine. A heteroaryl group of this invention may be substituted or unsubstituted.

As used herein, "alkoxy" refers to the formula —OR wherein R is an alkyl is defined as above, e.g. methoxy, ethoxy, n-propoxy, 1-methylethoxy (isopropoxy), n-butoxy, iso-butoxy, sec-butoxy, tert-butoxy, amoxy, tert-amoxy and the like.

As used herein, "alkylthio" refers to the formula —SR wherein R is an alkyl is defined as above, e.g. methylmercapto, ethylmercapto, n-propylmercapto, 1-methylethylmercapto (isopropylmercapto), n-butylmercapto, iso-butylmercapto, sec-butylmercapto, tert-butylmercapto, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

As used herein, "aryloxy" and "arylthio" refers to RO— and RS—, in which R is an aryl, such as but not limited to phenyl.

As used herein, "acyl" refers to an "RC(=O)—" group with R as defined above.

As used herein, "cycloalkyl" refers to a completely saturated (no double bonds) mono- or multi-cyclic hydrocarbon ring system. Cycloalkyl groups of this invention may range from $C_3$ to $C_{10}$, in other embodiments it may range from $C_3$ to $C_6$. A cycloalkyl group may be unsubstituted or substituted.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of this invention may be unsubstituted or substituted.

As used herein, "halo" or "halogen" refers to F (fluoro), Cl (chloro), Br (bromo) or I (iodo).

As used herein, "halogenated alkyl" refers to an alkyl group in which one or more of the hydrogen atoms are replaced by halogen. Such groups include but are not limited to, chloromethyl, fluoromethyl, difluoromethyl, trifluoromethyl and 1-chloro-2-fluoromethyl, 2-fluoroisobutyl.

As used herein, the term "guanidinium group" refers to a moiety having the formula:

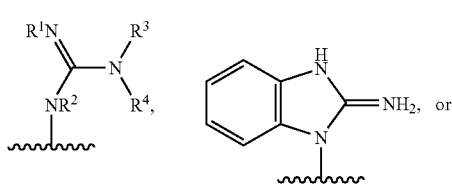

-continued

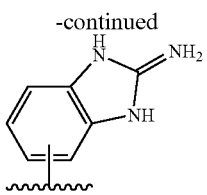

wherein $R^1$, $R^2$, $R^3$, and $R^4$ are as described above and the wavy line represent the point of attachment of the group to the rest of a molecule.

Whenever a group of this invention is described as being "optionally substituted" that group may be unsubstituted or substituted with one or more of the indicated substituents. Likewise, when a group is described as being "unsubstituted or substituted" if substituted, the substituent may be selected from the same group of substituents.

Compounds

One embodiment disclosed herein includes a compound of Formula (I):

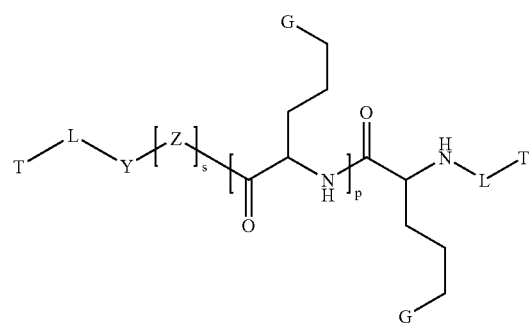

(I)

wherein each T is a terminal group independently selected from the group consisting of hydrogen, an alkylcarbonyl, an amine, a carboxylic group, a N-terminal peptide, a group that forms an N-terminal peptide bond, a C-terminal peptide, a group that forms a C-terminal peptide bond, a reporting moiety, an imaging agent moiety, and a therapeutic moiety;

wherein Z has the structure:

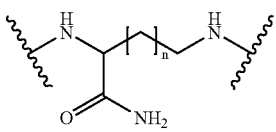

wherein s is 0 or 1;
wherein when s is 1, Y has the structure:

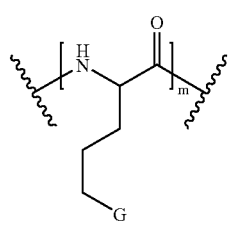

wherein when s is 0, Y has the structure:

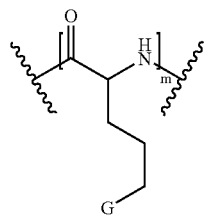

wherein m is an integer from 1 to 6;
wherein n is an integer from 0 to 10;
wherein p is an integer from 0 to 5;
wherein the sum of m and p is an integer from 6 to 11;
wherein each G is separately selected to be a guanidinium group having the formula:

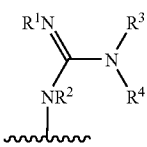

wherein the point of attachment of G is through a nitrogen atom or through $R^2$ or each G is separately selected from the group consisting of:

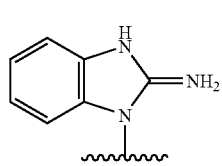 and 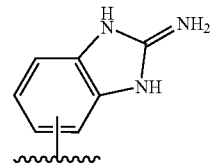

wherein:
each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;

each $R^1$ is optionally bound to the $R^2$, $R^3$, or $R^4$ on the same guanidinium group to form a heterocyclic ring;

each $R^2$ is optionally bound to the $R^3$ or $R^4$ on the same guanidinium group to form a heterocyclic ring; and each $R^3$ is optionally bound to the $R^4$ on the same guanidinium group to form a heterocyclic ring; and wherein each L is a linker moiety independently selected from the group consisting of mono-substituted, poly-substituted or unsubstituted variants of the following residues: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group, or L is absent.

In some embodiments, each G is separately selected from the group consisting of:

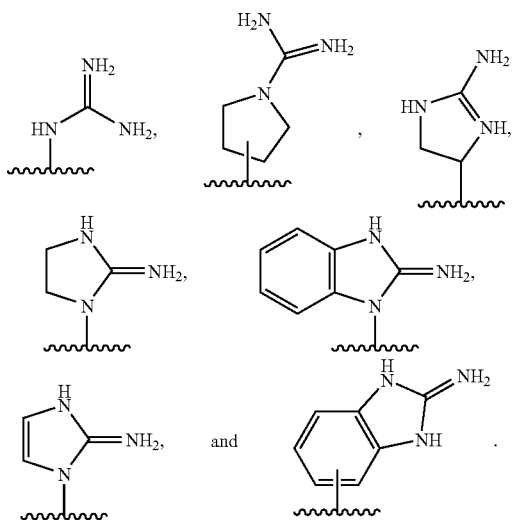

In some embodiments, $R^1$, $R^2$, $R^3$, and $R^4$ are hydrogen.

In other embodiments, at least one T can be a reporting moiety, an imaging agent moiety, or a therapeutic moiety. In some embodiments, at least one T can be a peptide nucleic acid. In other embodiments, at least one T can have the formula:

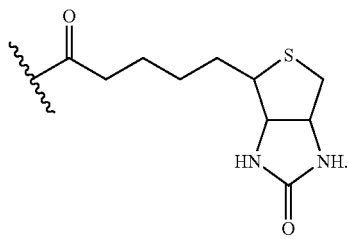

In yet still other embodiments, at least one T can have the formula:

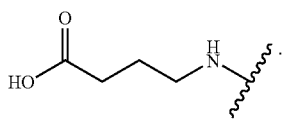

In some embodiments, at least one T can be a polypeptide. In other embodiments, at least one T can be a protein antigen. In still other embodiments, at least one T can be a tumor antigen. In yet still embodiments, at least one T can be a tisane moiety. In some embodiments, at least one T can be a metal ion. In other embodiments, at least one T can be an antimicrobial agent. In yet still other embodiments, at least one T can be an epitope tag (e.g., CYPYDVPDYA). In some embodiments, the therapeutic moiety can be an anti-cancer agent. Specifically, in another embodiment, the anti-cancer agent may be an anti-tumor agent. More specifically, in still another embodiment, the anti-tumor agent can be doxorubicin or a platinum metal complex. An exemplary platinum metal complex is the following:

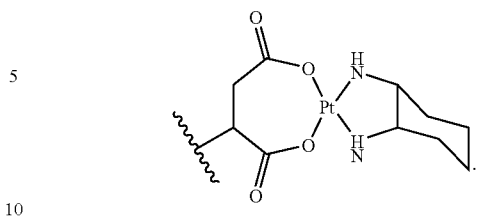

In some embodiments, at least one T can be an imaging agent moiety. In certain embodiments, the imaging agent moiety can be a gadolinium metal complex. An exemplary gadolinium metal complex is the following:

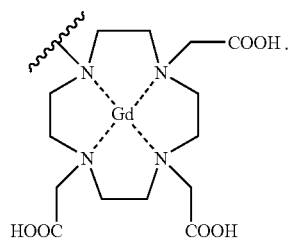

With respect to the linker moiety (L), in one embodiment, each L may be independently selected from the group consisting of mono-substituted, poly-substituted or unsubstituted variants of the following residues: $C_1$-$C_{12}$ alkyl, $C_2$-$C_{12}$ alkenyl, $C_2$-$C_{12}$ alkynyl, $C_1$-$C_{12}$ heteroalkyl, $C_2$-$C_{12}$ heteroalkenyl, $C_2$-$C_{12}$ heteroalkynyl, amide, ester, and disulfide group. In another embodiment, each L may be independently selected from the group consisting of mono-substituted, poly-substituted or unsubstituted variants of the following residues: $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, amide, ester, and disulfide group. In still another embodiment, each L may be independently selected from the group consisting of: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group optionally substituted with substituents selected from the group consisting of halogen, acyl, alkoxy, cycloalkoxy, aryl, heteroaryl, arylalkoxy carbonyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl. In some embodiments, the linker can have a first cleavable group and a second cleavable group, wherein when the first cleavable group is cleaved, the first cleavable group is converted to a nucleophilic moiety that is adapted to react with the second cleavable group. In some embodiments, the first group can be an amide group and the second group can be an ester group, and cleavage of the amide group yields a free amino group that reacts with the ester group. In some embodiments, the first group can be a phosphate ester group and the second group can be a carboxylate ester group, and cleavage of the phosphate ester group yields a free hydroxyl group that reacts with the carboxylate ester group.

In one embodiment, a compound of Formula (I) can have the following structure:
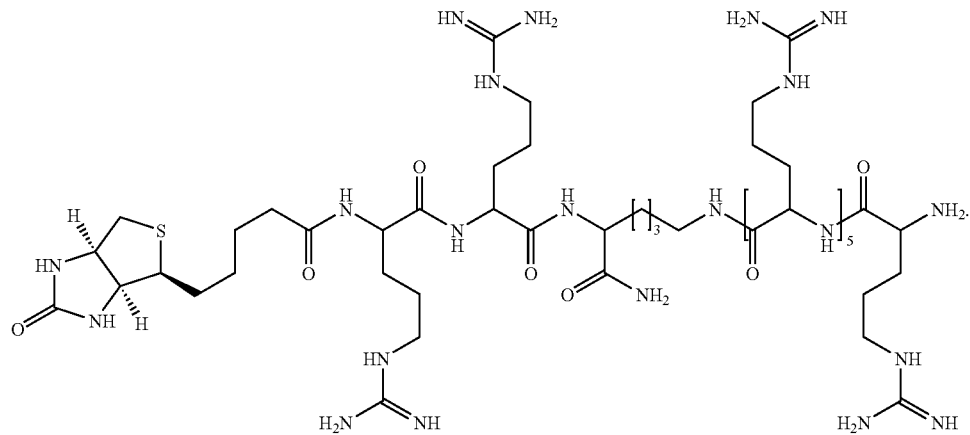
25
In another embodiment, a compound of Formula (I) can have the following structure:
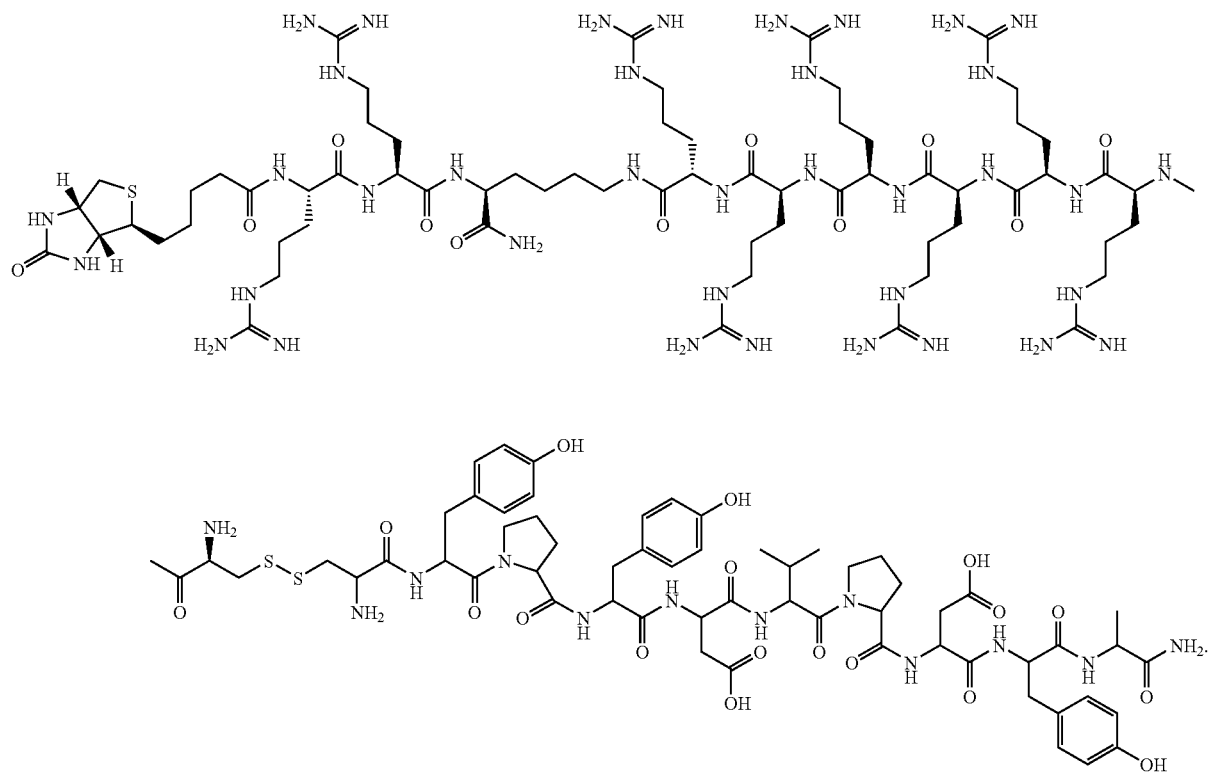

In still another embodiment, a compound of Formula (I) can have the following structure:

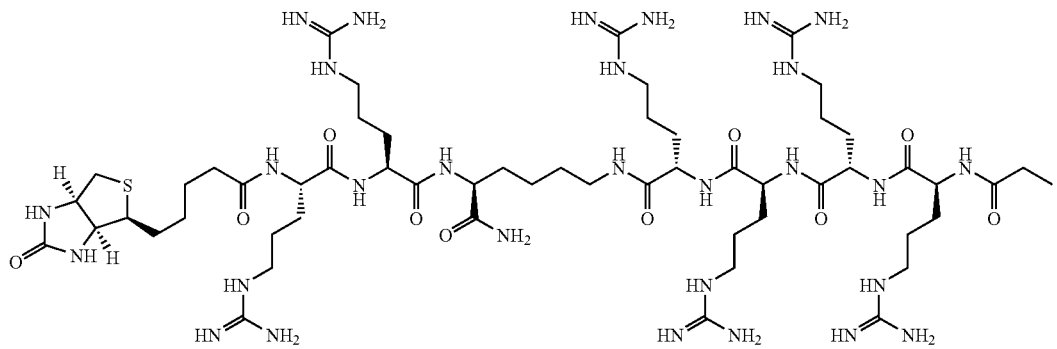

Another embodiment disclosed herein includes a compound of Formula (II):

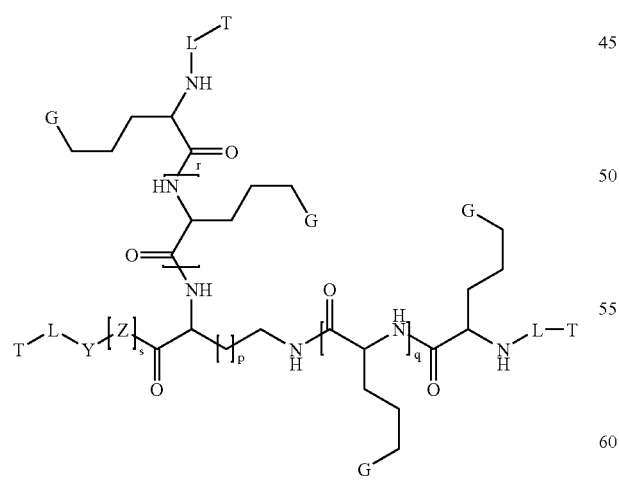

(II)

wherein each T is a terminal group independently selected from the group consisting of hydrogen, an alkylcarbonyl, an amine, a carboxylic group, a N-terminal peptide or group that forms an N-terminal peptide bond, a C-terminal peptide or group that forms a C-terminal peptide bond, a reporting moiety, an imaging agent moiety, and a therapeutic moiety;

wherein Z has the structure:

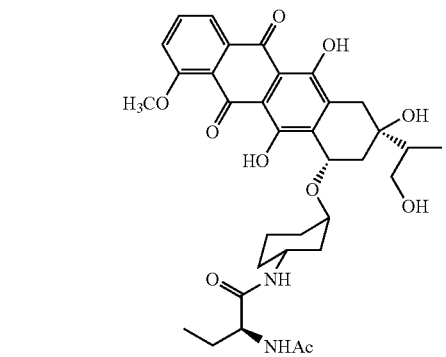

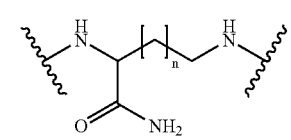

wherein s is 0 or 1;

wherein when s is 1, Y has the structure:

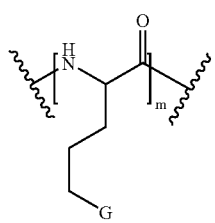

wherein when s is 0, Y has the structure:

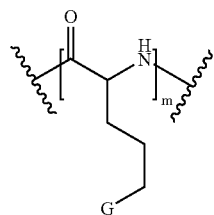

wherein p is an integer from 0 to 10;
wherein q is an integer from 0 to 5;
wherein r is an integer from 0 to 5;
wherein m is an integer from 1 to 6;
wherein n is an integer from 0 to 10;
wherein the sum of m, q, and r is an integer from 6 to 16;
wherein each G is separately selected to be a guanidinium group having the formula:

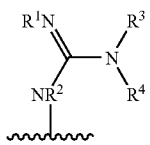

wherein the point of attachment of G is through a nitrogen atom or through $R^2$ or each G is separately selected from the group consisting of:

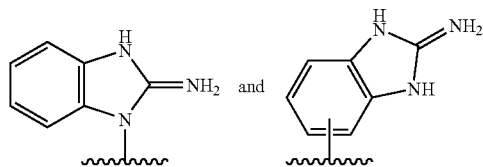

wherein:
each $R^1$, $R^2$, $R^3$, and $R^4$ are separately selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, and pentamethylchroman-6-sulfonyl;
each $R^1$ is optionally bound to the $R^2$, $R^3$, or $R^4$ on the same guanidinium group to form a heterocyclic ring;
each $R^2$ is optionally bound to the $R^3$ or $R^4$ on the same guanidinium group to form a heterocyclic ring; and
each $R^3$ is optionally bound to the $R^4$ on the same guanidinium group to form a heterocyclic ring; and
wherein each L is a linker moiety independently selected from the group consisting of mono-substituted, poly-substituted or unsubstituted variants of the following residues: $C_1$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group, or L is absent.

In some embodiments, each G is separately selected from the group consisting of:

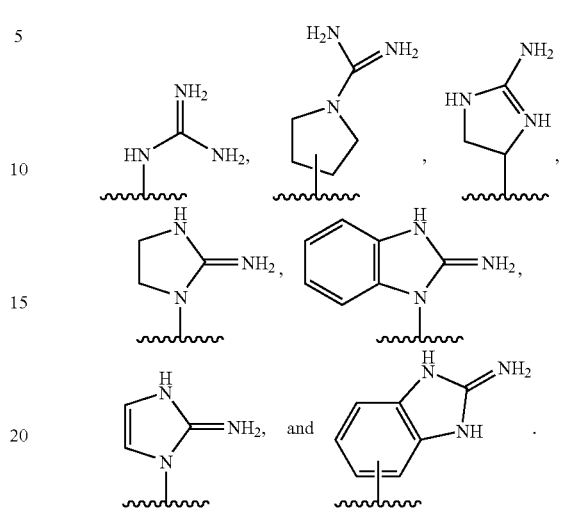

In some embodiments, $R^1$, $R^2$, $R^3$, and $R^4$ are hydrogen.

In other embodiments, at least one T can be a reporting moiety, an imaging agent moiety, or a therapeutic moiety. In some embodiments, at least one T can be a peptide nucleic acid. In other embodiments, at least one T can have the formula:

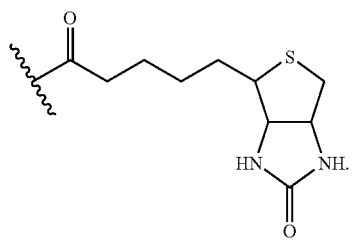

In yet still other embodiments, at least one T can have the formula:

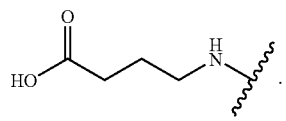

In some embodiments, at least one T can be a polypeptide. In other embodiments, at least one T can be a protein antigen. In still other embodiments, at least one T can be a tumor antigen. In yet still embodiments, at least one T can be a tisane moiety. In some embodiments, at least one T can be a metal ion. In other embodiments, at least one T can be an antimicrobial agent. In yet still other embodiments, at least one T can be an epitope tag (e.g., CYPYDVPDYA). In some embodiments, the therapeutic moiety can be an anti-cancer agent. Specifically, in another embodiment, the anti-cancer agent may be an anti-tumor agent. More specifically, in still another embodiment, the anti-tumor agent can be doxorubicin or a platinum metal complex. An exemplary platinum metal complex is the following:

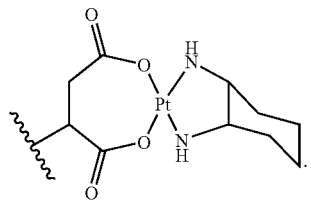

In some embodiments, at least one T can be an imaging agent moiety. In certain embodiments, the imaging agent moiety can be a gadolinium metal complex. An exemplary gadolinium metal complex is the following:

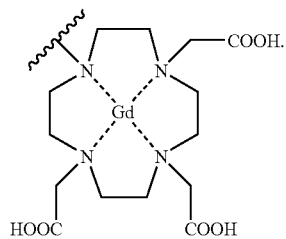

Referring to the linker moiety (L), in one embodiment, each L may be independently selected from the group consisting of mono-substituted, poly-substituted or unsubstituted variants of the following residues: $C_1$-$C_{12}$ alkyl, $C_2$-$C_{12}$ alkenyl, $C_2$-$C_{12}$ alkynyl, $C_1$-$C_{12}$ heteroalkyl, $C_2$-$C_{12}$ heteroalkenyl, $C_2$-$C_{12}$ heteroalkynyl, amide, ester, and disulfide group. In another embodiment, each L may be independently selected from the group consisting of mono-substituted, poly-substituted or unsubstituted variants of the following residues: $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, amide, ester, and disulfide group. In still another embodiment, each L may be independently selected from the group consisting of: $C_1$-$C_{24}$ alkyl, $C_2$-$C_{24}$ alkenyl, $C_2$-$C_{24}$ alkynyl, $C_1$-$C_{24}$ heteroalkyl, $C_2$-$C_{24}$ heteroalkenyl, $C_2$-$C_{24}$ heteroalkynyl, amide, ester, and disulfide group optionally substituted with substituents selected from the group consisting of halogen, acyl, alkoxy, cycloalkoxy, aryl, heteroaryl, arylalkoxy carbonyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl. In some embodiments, the linker can have a first cleavable group and a second cleavable group, wherein when the first cleavable group is cleaved, the first cleavable group is converted to a nucleophilic moiety that is adapted to react with the second cleavable group. In some embodiments, the first group can be an amide group and the second group can be an ester group, and cleavage of the amide group yields a free amino group that reacts with the ester group. In some embodiments, the first group can be a phosphate ester group and the second group can be a carboxylate ester group, and cleavage of the phosphate ester group yields a free hydroxyl group that reacts with the carboxylate ester group.

In one embodiment, the compound of Formula (II) can have the following structure:

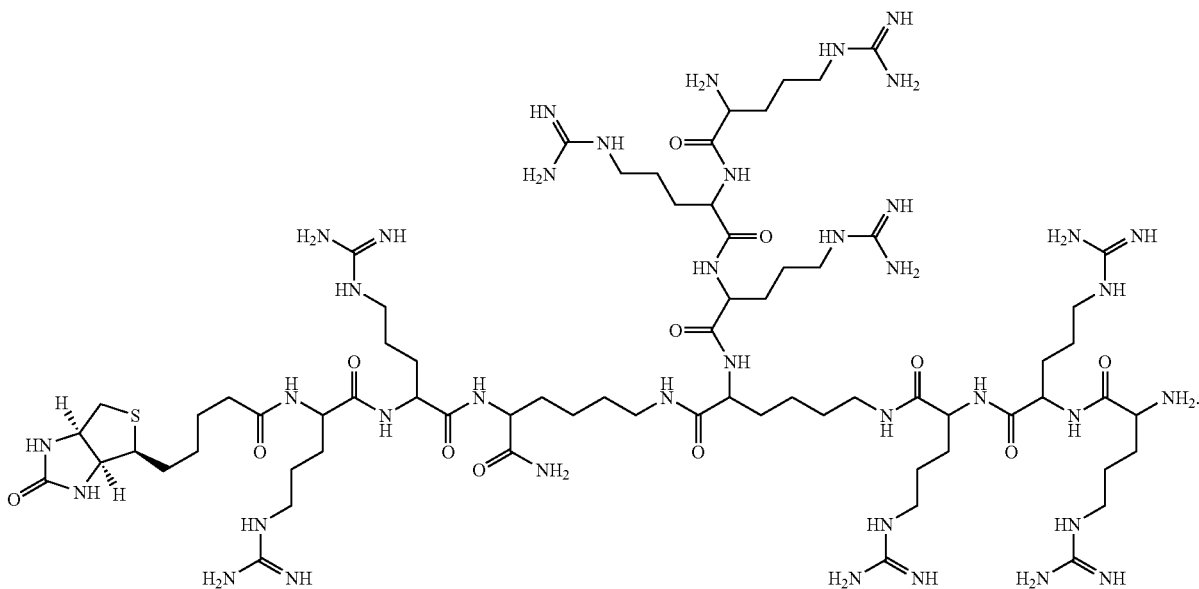

In another embodiment, the compound of Formula (II) can have the following structure:
In yet another embodiment, the compound of Formula (II) can have the following structure:
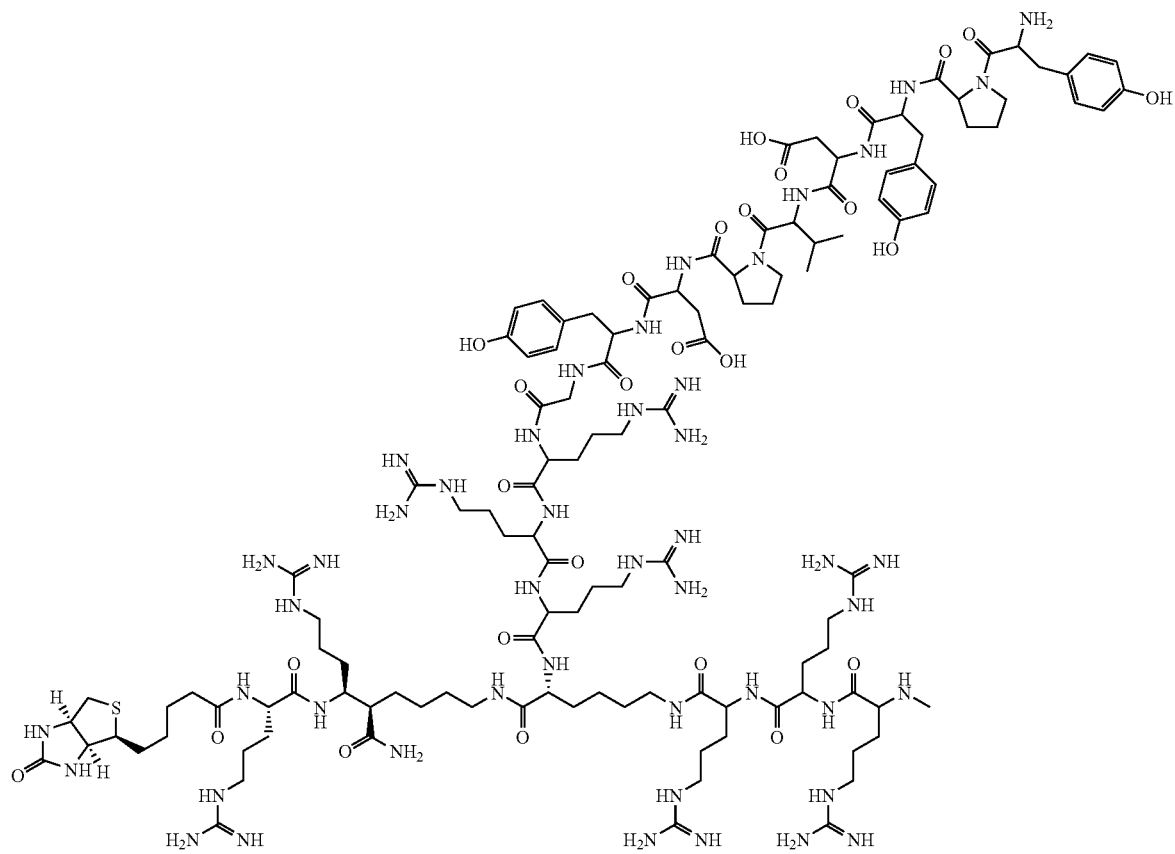
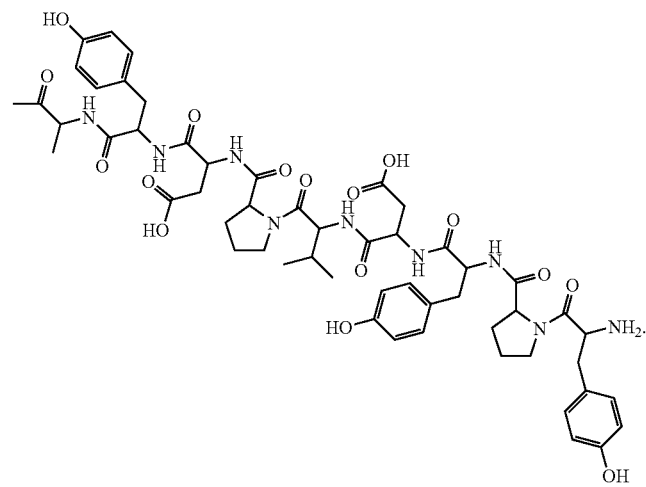

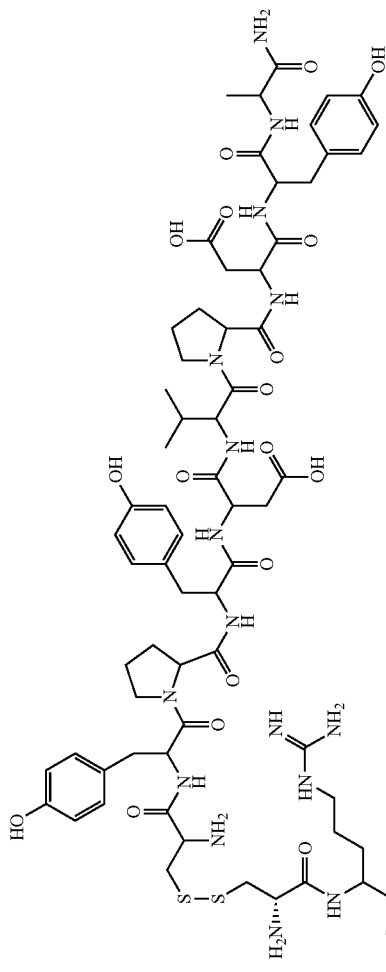
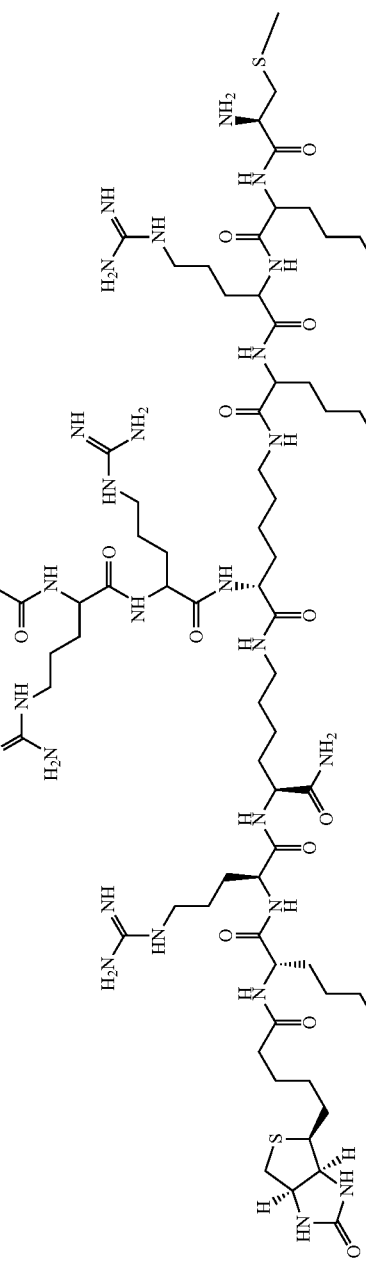
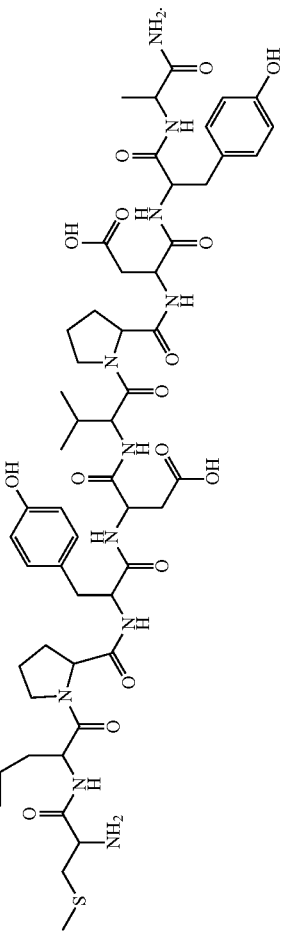

In still yet another embodiment, the compound of Formula (II) can have the following structure:
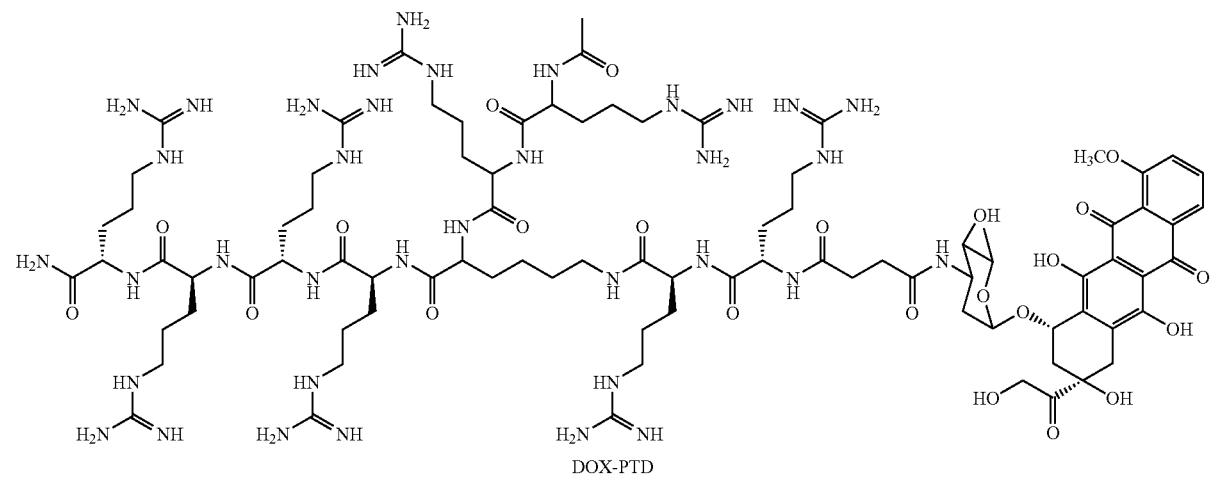
DOX-PTD
In another embodiment, the compound of Formula (II) can have the following structure:
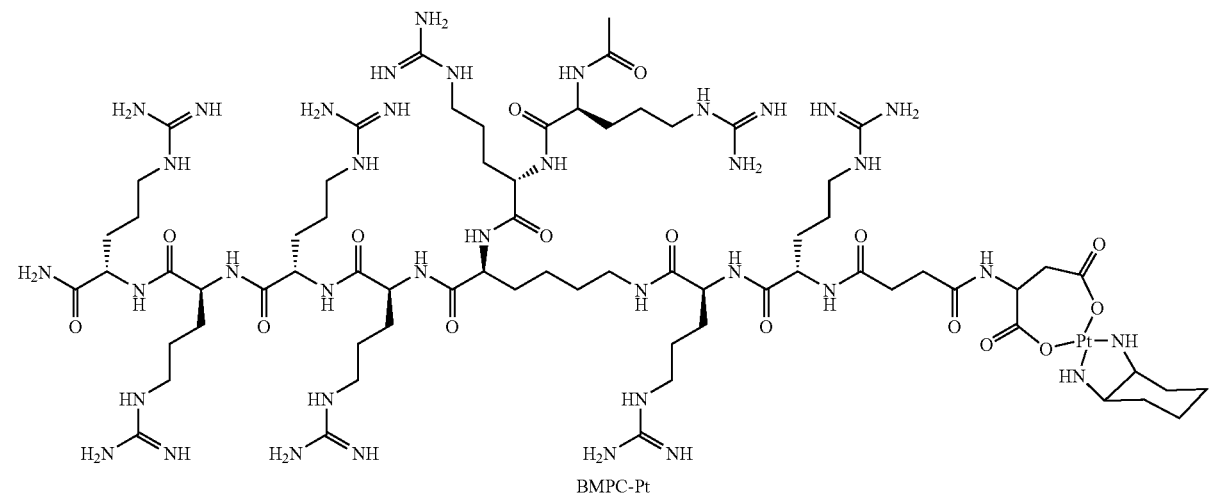
BMPC-Pt In still another embodiment, the compound of Formula (II) can have the following structure:

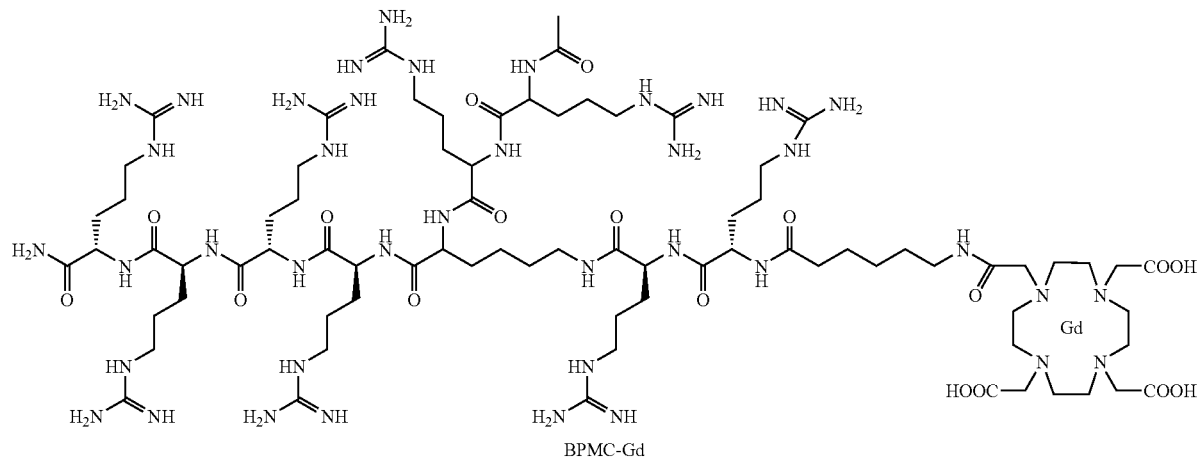

BPMC-Gd

Those of skill in the art will recognize that branching provides additional locations to attach terminal groups. Accordingly, in some embodiments, additional branching is provided than depicted in the structure above. Those of skill in the art will recognize the generalization of the structure above to produce a larger number of branch points.

Where the compounds disclosed herein have at least one chiral center, they may exist as a racemate or as enantiomers. It should be noted that all such isomers and mixtures thereof are included in the scope of the present invention. Furthermore, some of the crystalline forms for the compounds of disclosed herein may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

In some embodiments, the compounds disclosed herein may be provided in a pharmaceutically acceptable salt. The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

In various embodiments, the compounds disclosed herein can be used alone, in combination with other compounds disclosed herein, or in combination with one or more other agents that are therapeutically active.

Methods of Use

One embodiment disclosed herein includes a method for transporting a biologically active moiety across a biological membrane using the transporter molecules described above. Exemplary biologically active moieties include but are not limited to reporting moieties, imaging agent moieties, therapeutic moieties, and targeting moieties. In some embodiments, the contacting can be effective in promoting the transport of the biologically active moiety across the biological membrane at a rate that is greater than a trans-membrane transport rate of the biologically active moiety in non-conjugated form. In some embodiments, the transporter molecules described herein may be used to enhance transport of a drug across a cell membrane. In one embodiment, enhancing the transport of a drug across a cell membrane comprises linking a therapeutic moiety to the transporter molecule. The therapeutic moiety may be any suitable radical of a therapeutically effective drug. In some embodiments, the therapeutic moiety is linked to the transporter molecule via a linker such that when the molecule is within a cell; the therapeutic moiety is cleaved, generating the drug molecule. In some embodiments, a targeting moiety is also attached to the transporter molecule. The targeting moiety may be a moiety that preferentially binds to receptors on one or more cell types. Thus, the transporter molecule will have increased affinity to particular cell types, and thus increased transport across the membrane of those cell types. In this way, a drug can be effectively delivered specifically to the interior of cells where the drug will have its most beneficial effect.

In some embodiments, a method is provided for converting a drug to a form that is more bioavailable. The method may comprise linking the drug to a transporter molecule as described herein. The transporter molecule will exhibit enhanced transport across cellular membranes and thus the attached drug will be more bioavailable than when delivered alone.

In some embodiments, the cell membrane across which the transporter molecule passes is a eukaryotic cell membrane, such as the membrane in mammalian cells, cancer cells, insect cells, plant cells, or yeast cells. In other embodiments, the membrane is a prokaryotic cell membrane, such as bacteria cell membrane. In some embodiments, the transporter molecules described herein may similarly be used to enhance transport of a drug across epithelial tissue, such as across skin, mucosmembrane, and brain blood barriers.

Another embodiment disclosed herein describes a method of treating cancer comprising contacting a cancer cell in a subject with a compound having the structure of Formula (I) or (II), or a pharmaceutically acceptable salt and pro-drug ester thereof, whereby the contacting is effective to promote transport of the therapeutic moiety across the biological membrane of the cancer cell at a rate that is greater than a trans-membrane transport rate of the therapeutic moiety in non-conjugated form.

A non-limiting of cancers include prostate cancer, melanoma, breast cancer, ovarian cancer, lung cancer, pancreatic cancer, and colon cancer.

The term "subject" refers to an animal, preferably a mammal, and most preferably a human, who is the object of treatment, observation or experiment. Exemplary mammals include mice, rodents, hamsters, gerbils, rabbits, guinea pigs, dogs, cats, sheep, goats, cows, horses, giraffes, platypuses, primates, such as monkeys, chimpanzees, apes, and humans.

Some of the embodiments disclosed herein may further comprise identifying a subject in need of a therapeutic agent.

Methods of Preparation

The compounds disclosed herein may be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in Protective Groups in Organic Chemistry (ed. J. F. W. McOmie, Plenum Press, 1973); and Greene & Wuts, Protective Groups in Organic Synthesis, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, Comprehensive Organic Transformations, VCH Publishers, 1989, or L. Paquette, ed., Encyclopedia of Reagents for Organic Synthesis, John Wiley and Sons, 1995, which are both hereby incorporated herein by reference in their entirety.

The transporter molecules described herein may be prepared by linking together guanidinium group containing monomers and spacer unit monomers. Spacer unit monomers may be synthesized by techniques known in the art. In some embodiments, spacer unit monomers containing amine and carboxylic terminal groups may be synthesized using techniques known in the art.

The guanidinium group containing monomers may be synthesized by techniques known in the art. In some embodiments, the guanidinium group containing monomers are arginine residues or derivatives thereof.

Formation of the polymers containing the guanidinium and spacer unit monomers may be obtained by using commercially available solid phase techniques. For example, the polymer may be grown on a Rink Amide MBHA resin. The resin can be reacted with piperdine-DMF to deprotect the amine. The deprotected amine can then be reacted with Fmoc-Arg(Pbf)-OH/HBTU/HOBt/DIPEA in DMF to add a guanidinium containing peptide. These steps can be repeated as many times as necessary to add the desired number of guanidinium containing peptides. If Z is present in the compound, the Z unit is added by reacting the deprotected amine with a reagent such as Fmoc-Lys(Mtt)-OH/HBTU/HOBt/DIPEA in DMF. Additional guanidinium containing peptides can then be added to the Z unit as described above.

If a compound of Formula (II) is desired, the Rink Amide MBHA resin with added guanidinium containing peptides can be reacted with a reagent such as Fmoc-Lys(Mtt)-OH/HBTU/HOBt/DIPEA in DMF. The resulting compound is then reacted with $Ac_2O$/DIPEA in DMF and TFA-DCM. Guanidinium containing peptides can then be added to form the branched portion of the transporter molecule using piperdine-DMF followed by and Fmoc-Arg(Pbf)-OH/HBTU/HOBt/DIPEA in DMF. These steps can be repeated as many times as necessary to add the desired number of guanidinium containing peptides.

After forming the transporter molecule, the desired biologically active moiety can then be conjugated to the transporter molecule. For example, in some embodiments, the transporter molecule can be conjugated to an appropriate linker (e.g., a succinic linker) and then a therapeutic moiety such as doxorubicin hydrochloride can be combined with the transporter molecule. If desired, a reporting moiety such as biotin can also be conjugated to the transporter molecule under appropriate conditions (e.g., biotin/HBTU/HOBt/DIPEA in DMF). An imaging agent moiety (e.g., a gadolium metal complex) can also be conjugated to the transporter molecule. The resin can be cleaved before or after adding the linker, or before or after adding the therapeutic moiety using TFA/$H_2O$/TIS.

Although the polymer linkages in the method described above involve formation of peptide bonds, those of skill in the art will recognize other functional groups that could be used to form linkages between the monomer units of the molecule, such as by forming ester bonds between the monomers.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

Pharmaceutical Compositions

In another aspect, the present disclosure relates to a pharmaceutical composition comprising physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethy cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica,* 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.,* 10(1):29-45 (1994)), lipid-soluble formulations (Alm et al., *Prog. Clin. Biol. Res.,* 312:447-58 (1989)), and microspheres (Mordenti, *Toxicol. Sci.,* 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others:, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the therapeutic moiety incorporated, the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

The following examples serve to illustrate the present invention and are not, in any way, intended to be considered limitations thereof.

EXAMPLES

Example 1

Synthesis of an Asymmetric Linear Oligomer

Linear peptides were synthesized using solid phase techniques on commercially available Rink Amide MBHA resins and Fmoc protected amino acids, according to methods well known in the art. Peptides were purified using C18 reverse phase HPLC columns and $CH_3CN$/aq. 0.1% TFA gradient elution and their structures were confirmed by mass spectrometry.

The following synthesis produced compound 9, an asymmetric linear oligomer having a biotin terminal group. Biotin was used to test transduction as described below.

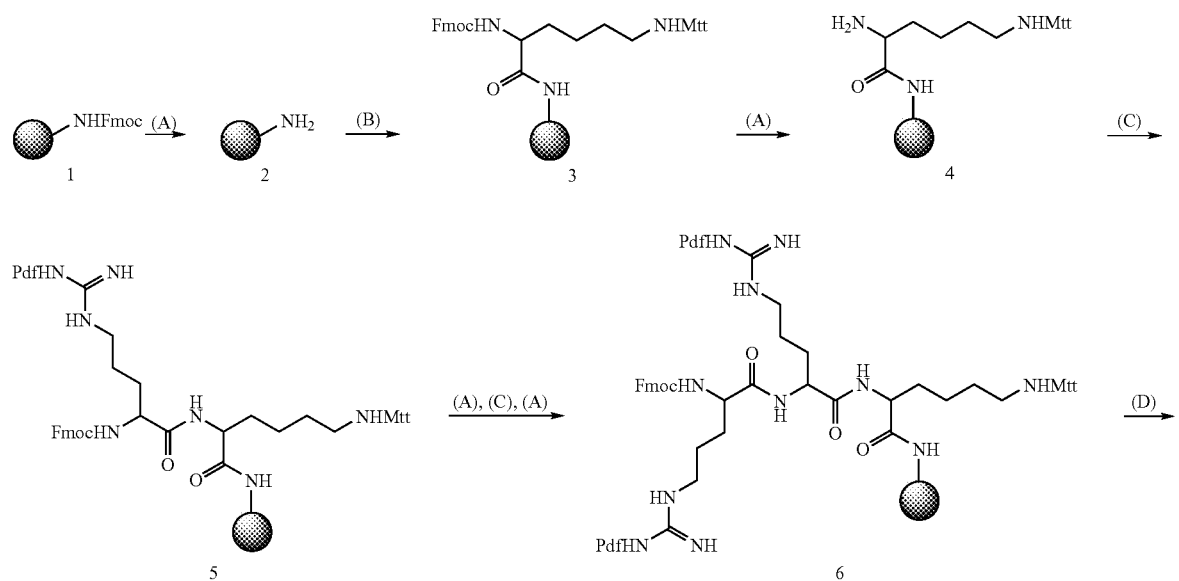

-continued
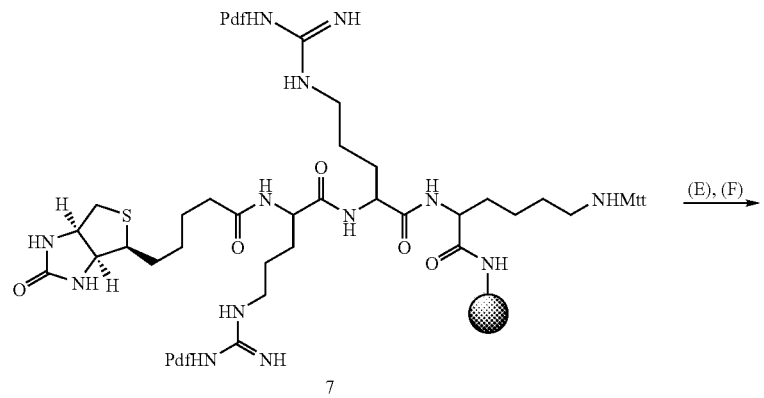
7
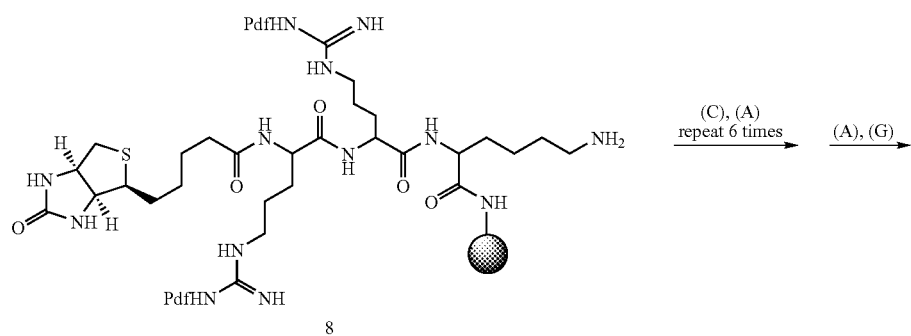
8
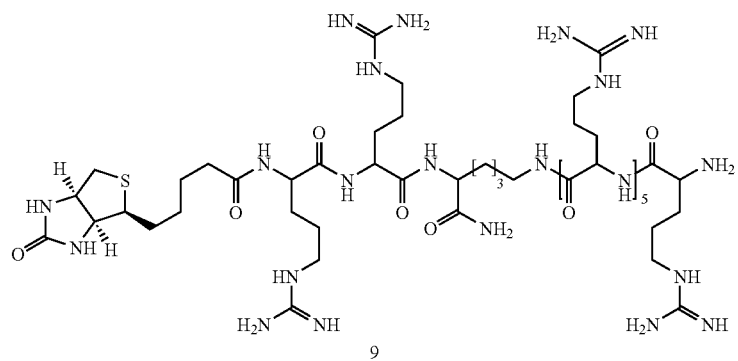
9
A. 20% Piperidine/DMF; B. Fmoc-Lys(Mtt)-OH, HBTU, HOBt, DIPEA, DMF; C. Fmoc-Arg(Pbf)-OH, HBTU, HOBt, DIPEA, DMF; D. Biotin, HBTU, HOBt, DIPEA, DMF; E. Ac$_2$O/DIPEA/DMF (1:2:7); F. 1.0% TFA-DCM; G. TFA-H2O-TIS (95:2.5:2.5).

Example 2

Synthesis of Branched-Chain Oligomer

Branched peptides were synthesized using solid phase techniques on commercially available Rink Amide MBHA resins and Fmoc protected amino acids, according to methods well known in the art. Peptides were purified using C18 reverse phase HPLC columns and CH₃CN/aq. 0.1% TFA gradient elution and their structures were confirmed by mass spectrometry.

The following synthesis produced compound 11, a branched-chain oligomer having a biotin terminal group. Biotin was used to test transduction as described below.

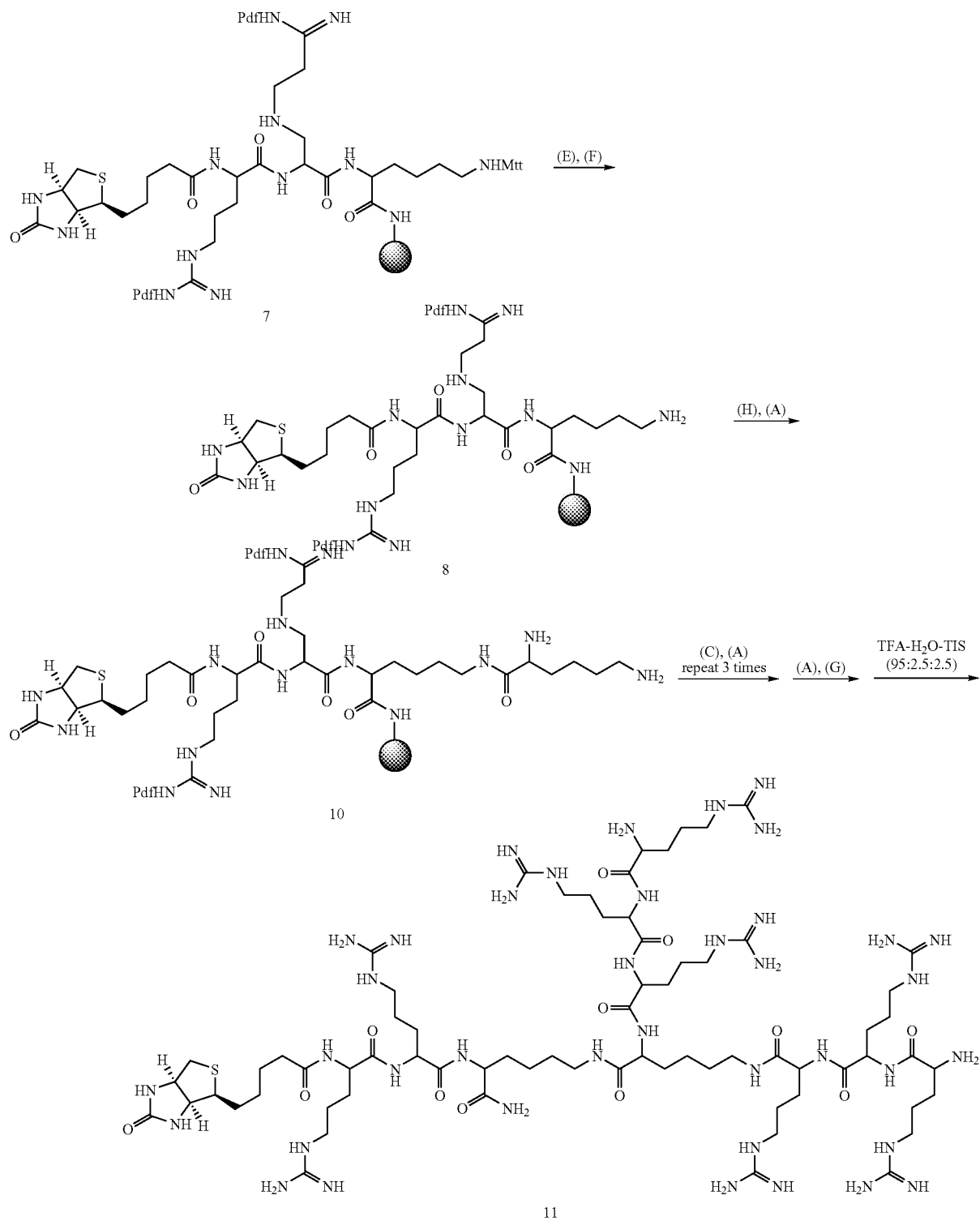

A. 20% Piperidine/DMF; B. Fmoc-Lys(Mtt)-OH, HBTU, HOBt, DIPEA, DMF; C. Fmoc-Arg(Pbf)-OH, HBTU, HOBt, DIPEA, DMF; D. Biotin, HBTU, HOBt, DIPEA, DMF; E. Ac₂O/DIPEA/DMF (1:2:7); F. 1.0% TFA-DCM; G. TFA-H₂O-TIS (95:2.5:2.5); H. Fmoc-Lys(Fmoc)-OH, HBTU, HOBt, DIPEA, DMF.

Example 3

Direct Conjugation with Cargo Moiety

The branched oligomer of Example 2 was coupled via peptide linkage to two HA epitope tags having the sequence CYPYDVPDYA at separate attachment points to produce the following molecule:

Example 4

Conjugation with Cargo Through Disulfide Linkages

The compound of Example 1 was conjugated to an HA moiety through a disulfide linkage by the following scheme:

The epitope tags facilitated identification of biomembrane penetration during in vitro and in vivo studies.

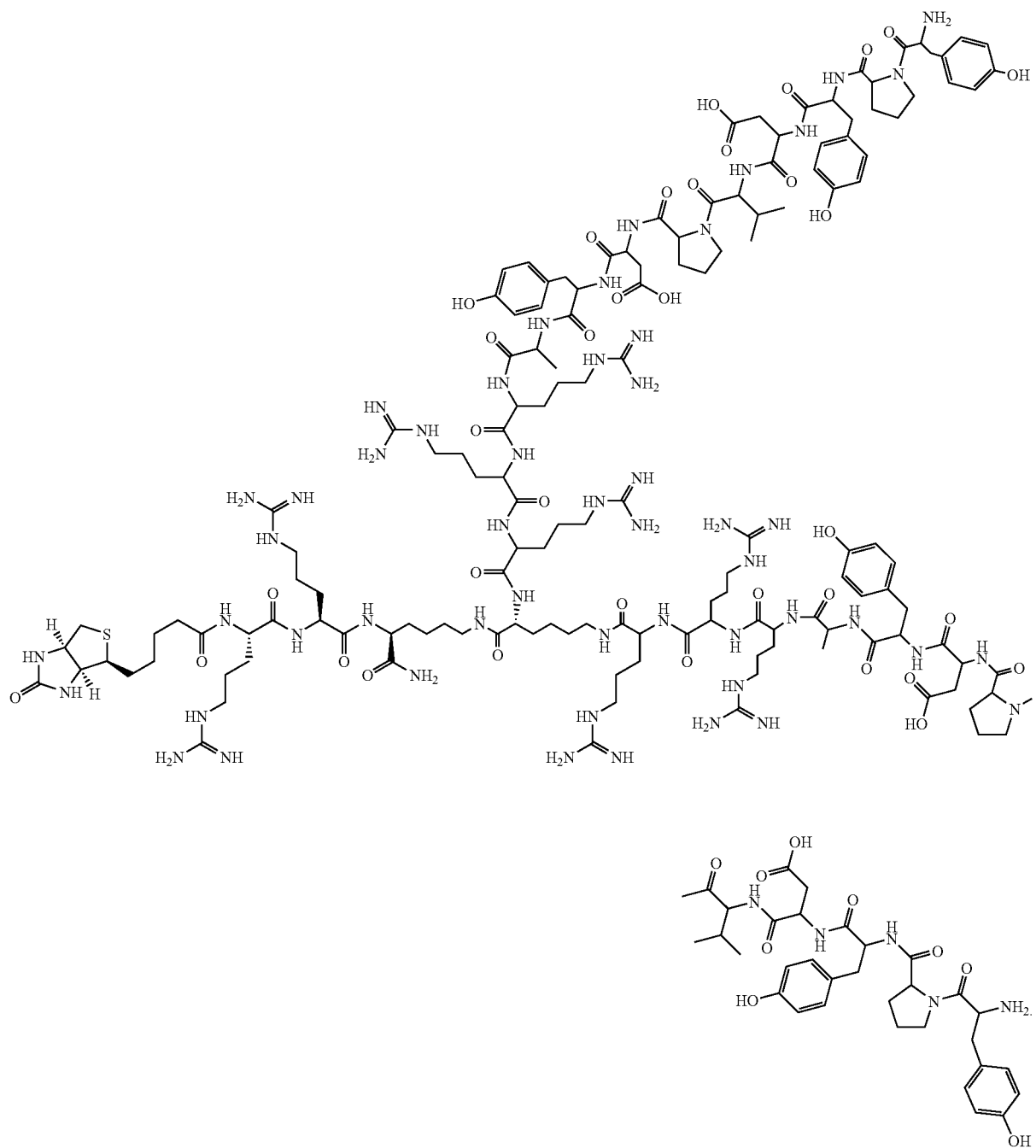

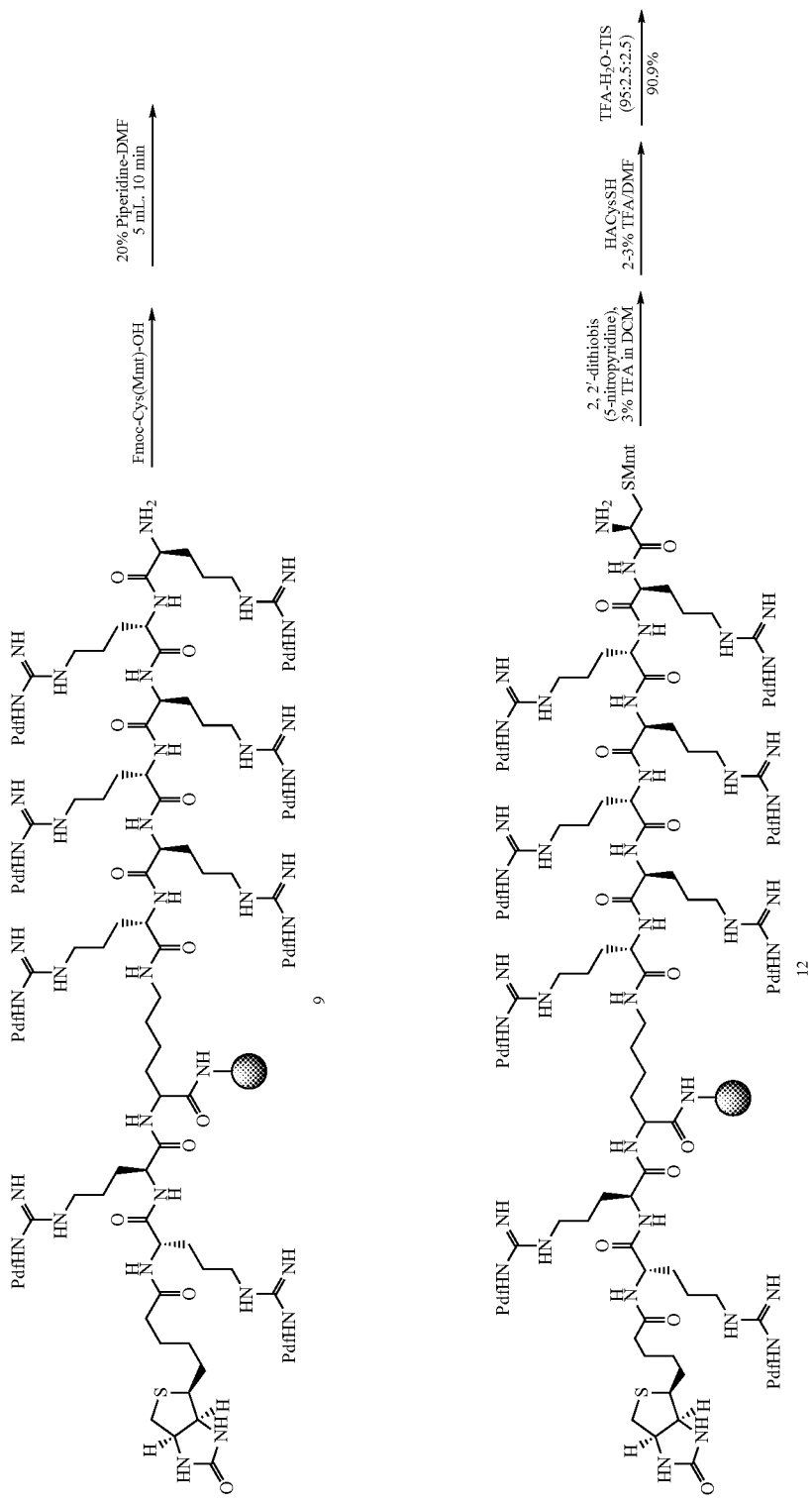

-continued
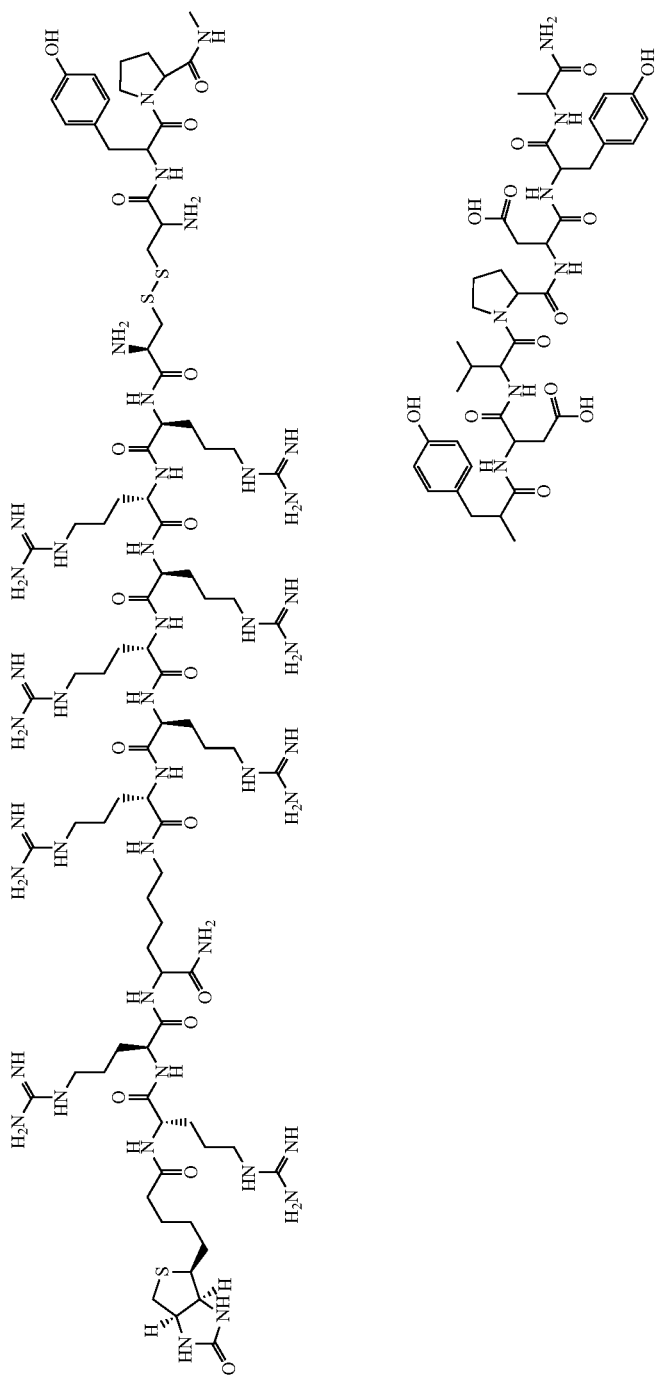
13

Loaded beads (50 mg, 0.025 mmol) were swelled in DCM and 3% TFA. 2,2'-dithiobis(5-nitropyridine) (5-10 eq) was added at room temperature. The mixture was mixed in a shaker overnight and then filtered and washed three times with DCM. R7CysSMmt (5 eq) in 10 mL of DCM (3% TFA) was then added and mixed in a shaker for another 12 hours. The beads were filtered and washed with DCM (3×20 mL) and dried under reduced pressure. The crude heterodisulfide product was obtained after TFA (95%) cleavage.

The compound of Example 2 was linked to two HA moieties through disulfide linkages through the following scheme:

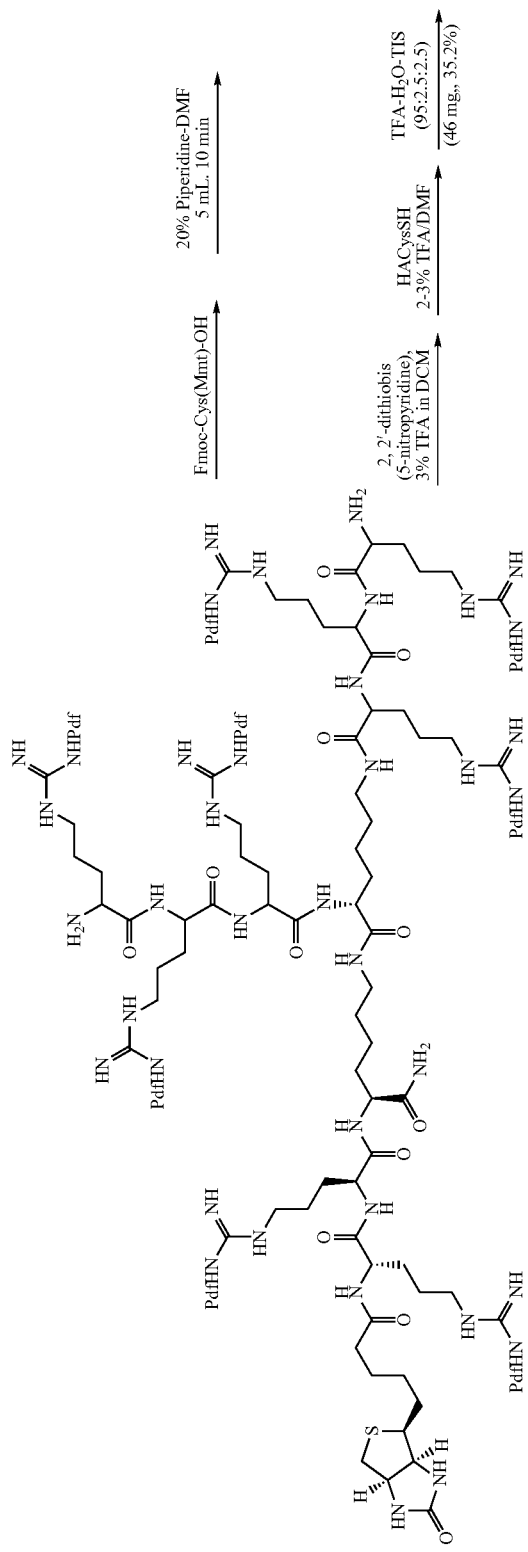

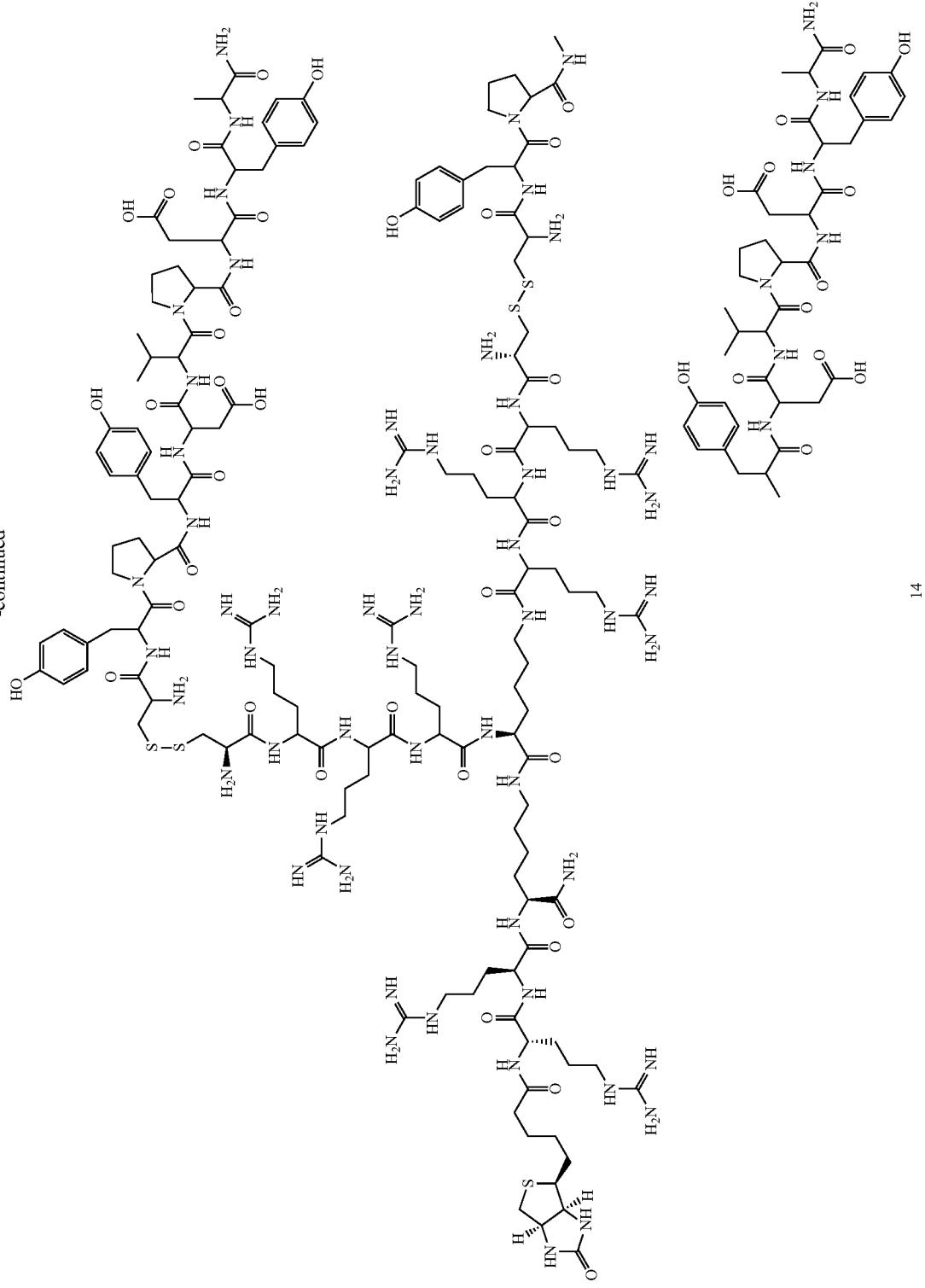

Example 5

Synthesis of DOX-PTD

As shown in FIGS. 1A and 2B, Doxorubicin-Protein transduction domain (DOX-PTD) 16 was synthesized starting from compound 15, which was generated according to FIGS. 1A, by using solid phase synthesis techniques. A succinic linker was added using DIPEA in DMF. Doxorubicin hydrochloride was then conjugated to the succinic linker using HBTU/HOBt/DIPEA in DMF. Compound 16 was then cleaved from the resin using TFA:TIS:H2O (95:2.5:2.5). The compound 16 was purified by reverse phase HPLC-prep and the product was collected in fractions which were confirmed by MALDI-TOF mass spectrometry.

Example 6

Synthesis of BMPC-Pt

Figure 2:
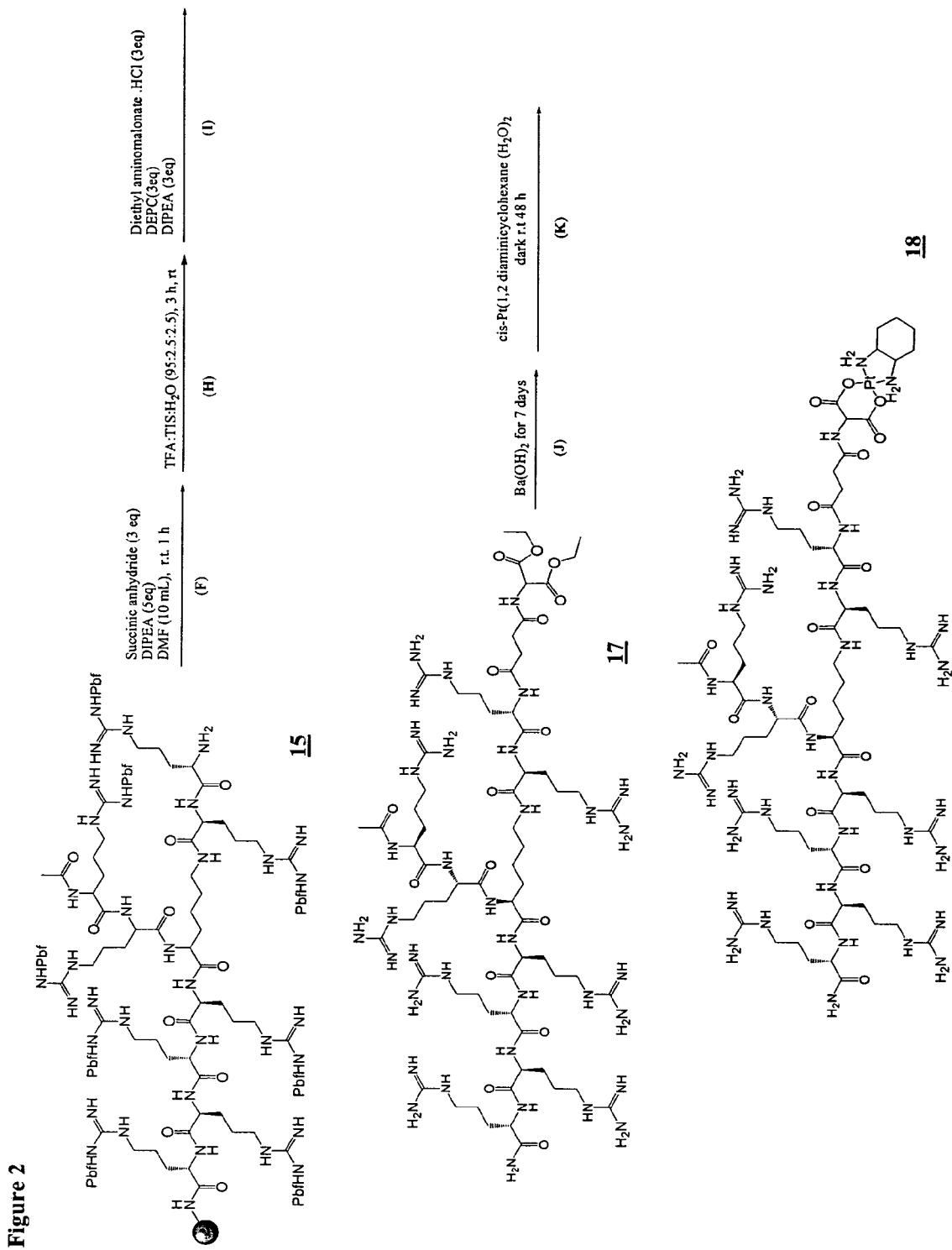
FIG. 2 shows a method for synthesizing Biomembrane Penetration Carrier-Platinum (BMPC-Pt).

As shown in FIG. 2, Biomembrane Penetration Carrier-Platinum (BMPC-Pt) 18 was synthesized starting from Compound 15 by using solid phase synthesis techniques. A succinic linker was added using DIPEA in DMF. The resin was cleaved using TFA:TIS:H2O (95:2.5:2.5). Diethyl aminomalonate was then conjugated to the succinic linker using DEPC(3 eq) and DIPEA (3 eq). One equivalent of Ba(OH)$_2$.8H2O was added to a solution of 17 (1 eq) in milipore water and stirred for 7 days. After 7 days, a suspension of cis-[DACHPtCl$_2$]•2H$_2$O (2 eq) in milipore water containing an equivalent amount of Ag$_2$SO$_4$ was added and the resulting solution was stirred for about 48 hours in the dark at room temperature under N$_2$. AgCl precipitated and was separated by filtration. The filtrate was transferred to the solution of BMPC aspartate barium salt and the reaction mixture was stirred overnight. The resulting compound was filtered and freeze dried. Compound 18 was crystallized from a water/acetone mixture as a white compound. Compound 18 was characterized by MALDI-TOF mass spectrometry.

Example 7

Synthesis of BMPC-Gd

Figure 3:
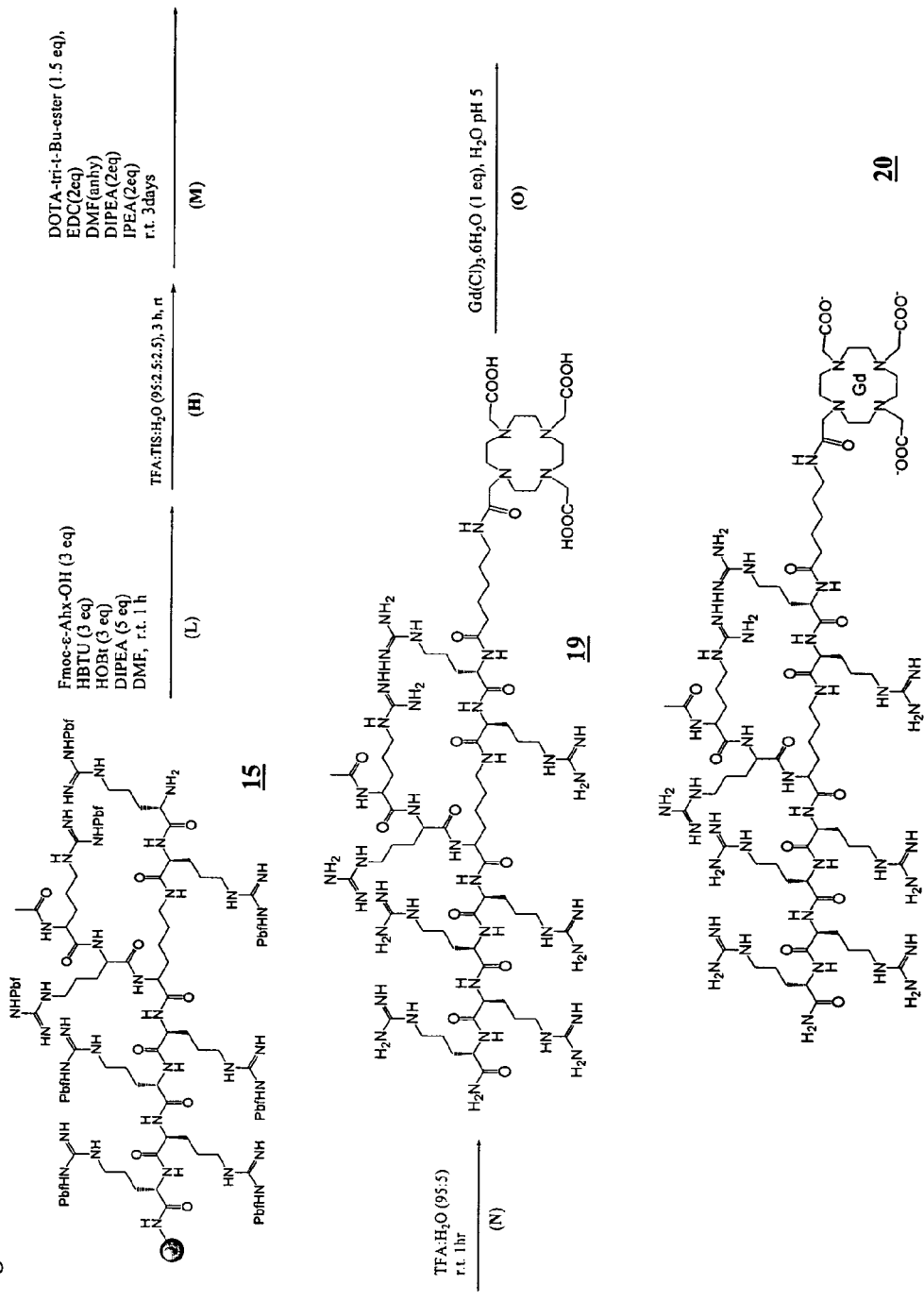
FIG. 3 shows a method for synthesizing Biomembrane Penetration Carrier-Gadolinium (BMPC-Gd).

As shown in FIG. 3, Biomembrane Penetration Carrier-Gadolinium (BMPC-Gd) was synthesized starting with Compound 15 by using solid phase synthesis techniques. A succinic linker was added using DIPEA in DMF and then cleaved from the resin by using a solution of TFA:TIS:H$_2$O (95:2.5:2.5). The crude intermediate was then conjugated to tri-tert-butyl 1,4,7,10-tetraazacyclododecane-1,4,7,10-tetraacetate (DOTA-tri-t-Bu-ester) (3 eq.). The t-butyl groups of DOTA-tri-t-Bu-ester were removed using TFA:H$_2$O (95:5) at room temperature for 3 hours. The resulting Compound 19 was purified by HPLC and characterized by MALDI-TOF mass spectrometry. One equivalent of compound 19 was added to the solution of one equivalent of Gd(Cl)$_3$6H$_2$O in milipore water. The reaction mixture was stirred at a pH of 5 at room temperature overnight. The product 20 was then precipitated from a water/acetone mixture. The product 20 was purified by reverse phase HPLC-prep and confirmed by MALDI-TOF mass spectrometry.

Example 8

Transduction Assay (In Vitro)

The transduction efficiency of compound 9 from Example 1 and compound 11 from Example 2 were analyzed. Hela 705 cells were seeded at 1.5×10$^4$/well in 96-well plate and cultured overnight (about 70% confluenced). The media was discarded and the cells rinsed with PBS. Biotin-labeled test compounds (dissolved in PBS, pH: 7.4) were applied to culture(s) and incubated for 30 min at 37° C. The media was carefully discarded and the cells rinsed with PBS. The cells were fixed in freshly prepared 4% paraformaldehyde for 10 min at 4° C. The cells were rinsed and incubated with a blocking reagent (10% BSA containing 0.5% Triton X-100 in PBS) for 30 min at 37° C. The cells were again rinsed with PBS and incubated with Streptavidin-FITC for 30 min at room temperature. The cells were then rinsed with PBS and observed under fluorescence microscope.

Figure 4:
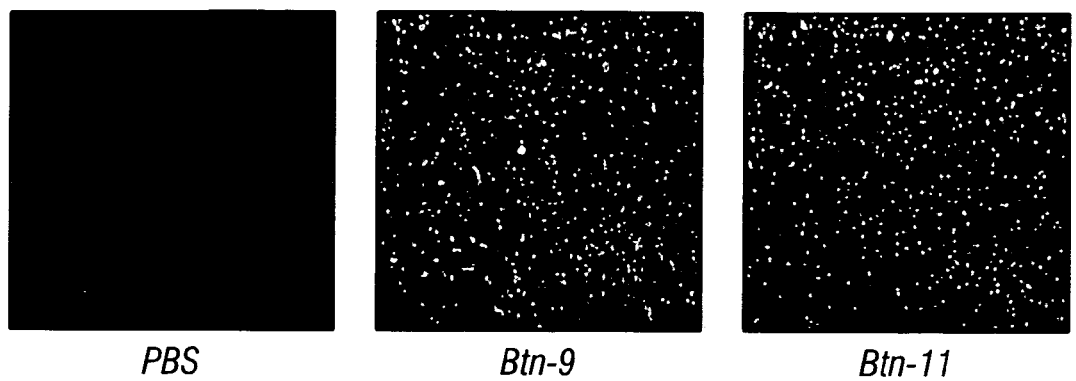
FIG. 4 depicts fluorescence microscope images of cells treated with protein domain transduction compounds.

FIG. 4 depicts the fluorescence microscope images of PBS control, compound 9, and compound 11. As shown in the images, both of biotin labeled 9 and 11 displayed dramatic transduction efficiency in Hela 705 cells compared to vehicle (PBS) treated group.

Figure 5:
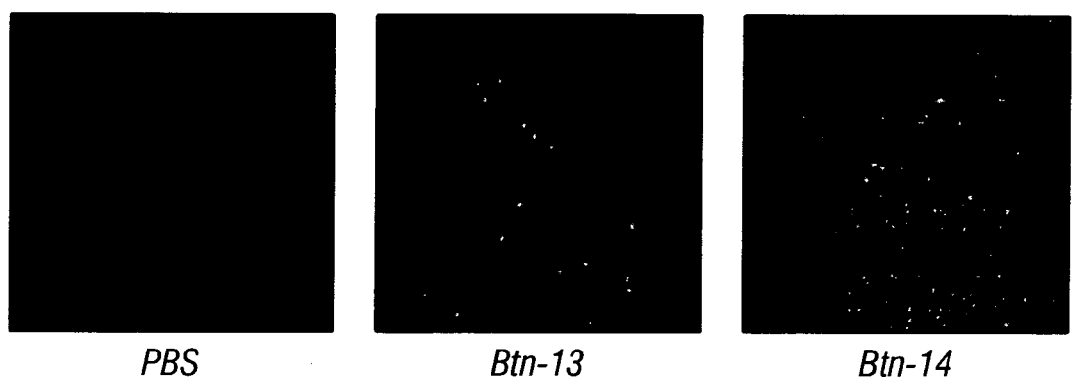
FIG. 5 depicts fluorescence microscope images of cells treated with protein domain transduction compounds containing disulfide-linked cargos.

The transduction activity of the disulfide linked HA compounds 13 and 14 from Example 4 were tested on Hela 705 cells following the procedure as mentioned above. FITC conjugated anti-HA antibody was applied for visualization. As shown in FIG. 5, both of biotin labeled 13 and 14 exhibited significant transduction efficiency in Hela 705 cells compared to vehicle (PBS) treated group.

Figure 6:
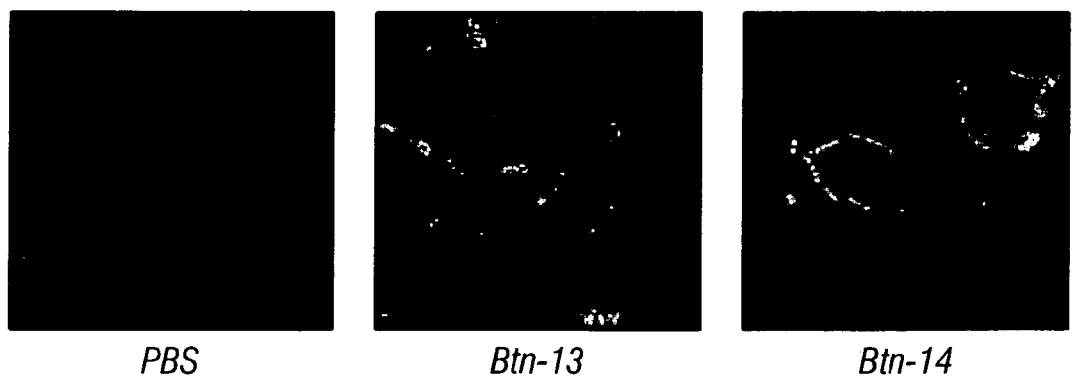
FIG. 6 depicts confocal images of cells treated with protein domain transduction compounds containing disulfide-linked cargos.

To elucidate intracellular delivery of 13 and 14, samples from the cell transduction assay described above were analyzed with confocal imaging technology. Blue color (stained with DAPI, from Sigma) visualized cell nucleus, red (stained with Phalloidin, from Sigma) outlined cell morphology, and green (FITC based staining with anti-HA antibody) showed the distribution of 13 and 14. FIG. 6 depicts the resulting images without color. The results indicated that both 13 and 14 displayed an intracellular distribution pattern.

Figure 7:
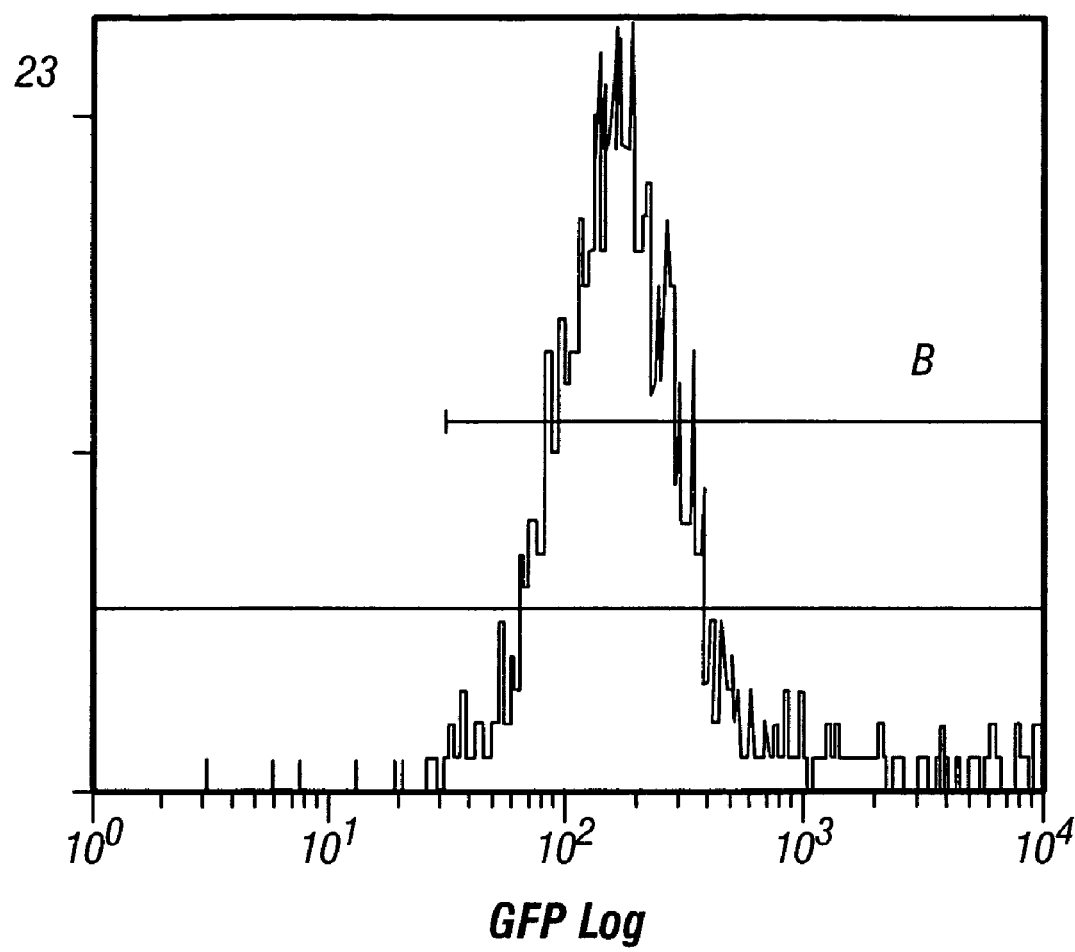
FIG. 7 depicts flow cytometry data protein domain transduction compounds containing disulfide-linked cargos.
Figure 8:
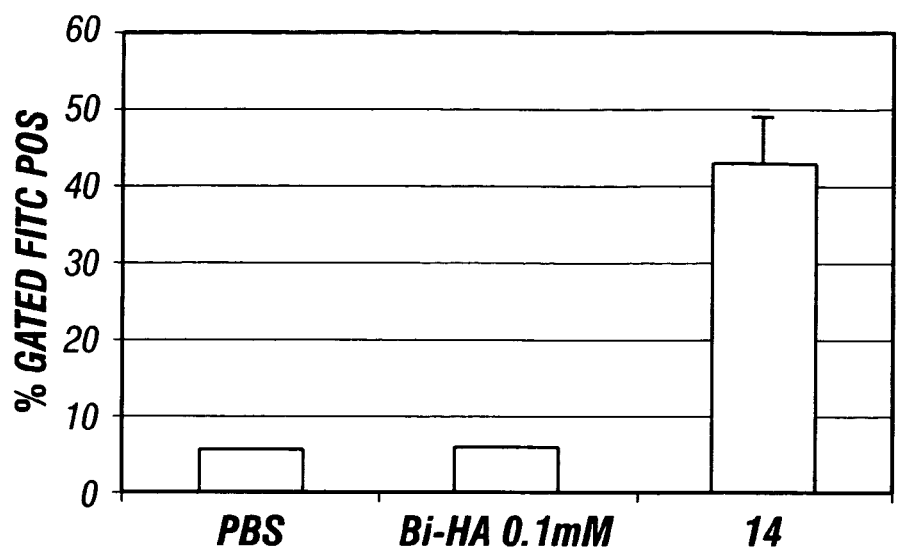
FIG. 8 is a bar graph depicting quantitative results from the flow cytometry data of FIG. 7.

To quantitatively analyze transduction efficiency, cell transduction samples were prepared for flow cytometry assay. Cell samples were collected as follows. Hela 705 cells were cultured on a 12-well plate. The media was discarded and the cells rinsed with PBS. Biotin labeled test compounds were applied to cell culture(s) and incubated for 30 min at 37° C. Media and was discarded and cells rinsed with PBS. Cells were fixed in freshly prepared 4% paraformaldehyde in PBS for 10 min at 4° C. The cells were then rinsed with PBS and incubated with a blocking reagent (10% BSA containing 0.5% Triton X-100 in PBS) for 30 min at 37° C. The cells were incubated with FITC-conjugated anti-HA antibody for 30 min at 37° C. and then rinsed with PBS. Cells were detached from the plate by incubation with Accutase™ solution. The cells were then gently suspended and collected into 1.5 ml tubes. The cells were spun down and the upper-layer Accutase™ solution was carefully discarded. 0.5 ml PBS was added into each tube and the cells re-suspended. Finally, a flow cytometry assay was performed. FIG. 7 depicts the cytometry assay data. This figure indicates that a portion of the cells were gated during the flow cytometry assay by translocation of the fluorescent dye tagged compounds. The quantitative results are depicted in FIG. 8 and demonstrate that compound 14 had significantly higher transduction efficiency (about 40% transduction) as compared to the PBS and biotin labeled HA controls (about 5% transduction).

Example 9

In Vivo Transdermal Experiments

Compounds 9 and 11 from Examples 1 and 2 were tested in vivo. In vivo evaluation was conducted with a transdermal delivery assay on nude mice (NU/NU ♀). Nude mice (female, 6 weeks old, from Charles River) were anesthetized with 50 μl cocktail of Ketaset 25 mg/ml, Xylazine 5 mg/ml (i.m.). The skin was wiped with saline and a 100 μl solution of the test compounds (1 mM in PBS) was applied. A plastic ring was used to isolate the test solution and vaseline was rubbed outside of the ring. After 30 min incubation, the animal was sacrificed under deep anesthesia and the skin was removed. Mouse skin tissue was immediately embedded in OTC medium, cut into 5 μm on a cryostat and collected on slides, and stored at −70° C. The tissue was fixed in freshly prepared 4% paraformaldehyde in PBS for 10 min at 4° C. The tissue was then rinsed in PBS 2×5 min and incubated with 10% BSA containing 0.5% Triton X-100 in PBS for 30 min at 37° C. The samples were incubated with Streptavidin-FITC (diluted in 1% BSA containing 0.05% Triton X-100 in PBS) overnight at 4° C. Following rinsing with PBS for 2×5 min, the tissue was incubated with cocktail of DAPI and Phalloidin in 1% BSA containing 0.05% Triton X-100 in PBS for 30 min at room temperature. The samples were rinsed twice in PBS 2×5 min and tap water and mounted with anti-fading mounting medium and observed under fluorescence microscope or confocal imaging analysis.

Figure 9:
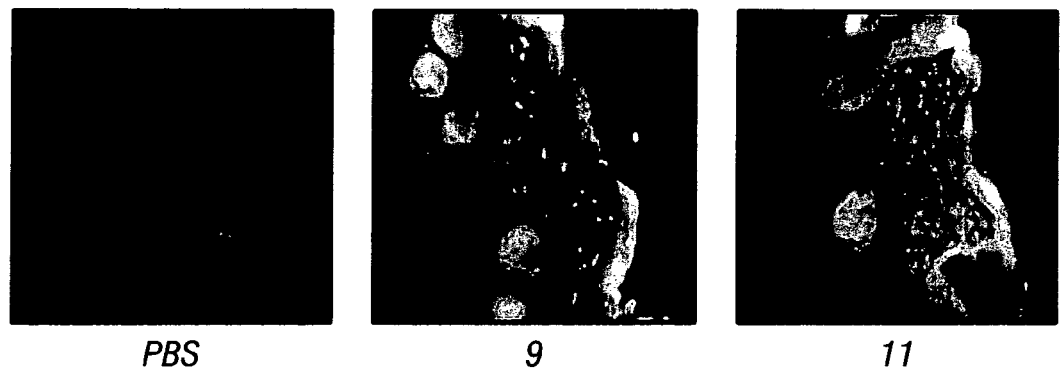
FIG. 9 depicts fluorescence microscope images of skin tissue treated with protein domain transduction compounds.
Figure 10:
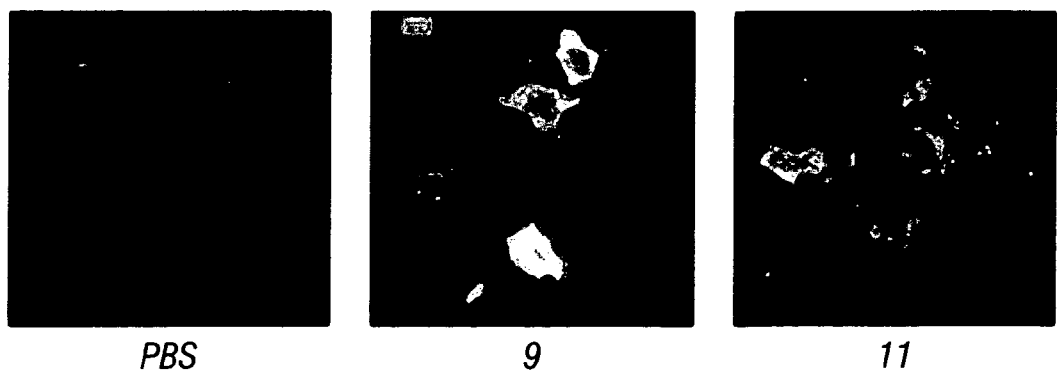
FIG. 10 depicts confocal images of skin tissue treated with protein domain transduction compounds.

FIG. 9 depicts the fluorescence microscope images and FIG. 10 depicts the confocal images. The images demonstrate that both compounds 9 and 11 displayed dramatic transdermal delivery efficiency compared to vehicle (PBS) treated tissue (FIG. 9). Confocal images (FIG. 10) showed intracellular distribution of PTD under high magnification.

Example 10

Cytotoxicity Assays

Prostate cancer cell lines (PC-3 cells) were maintained in 12-F medium containing 10% fetal bovine serum, 100 units/mL penicillin and 100 μg/mL streptomycin at 37° C. under 5% $CO_2$ and 100% humid condition. To avoid confluency due to the short doubling time (~20 hrs), the cells were split every 3-4 days.

The PC-3 cells were plated in 6-well tissue culture plates ($5 \times 10^5$ cells/well) and incubated overnight in 12-F medium with 10% FBS. For each well, an aliquot of 200 μl Doxorubicin-protein transduction domain (DOX-PTD) solution at same mole concentration (0.2 mg/per well) was added. The cells were then incubated at 37° C. in 5% $CO_2$ for 2 hrs.

After incubation, the live and dead cells were counted using cell staining analysis according to the protocol provided by the manufacturer. The dead cells stain red while the live cells stain green. The green and red fluorescent signals from the cells were observed under a fluorescent microscope (Olympus, filter 570 nm-605). The percentage of live cells in the cultures was determined from counts of three fields.

Figure 11:
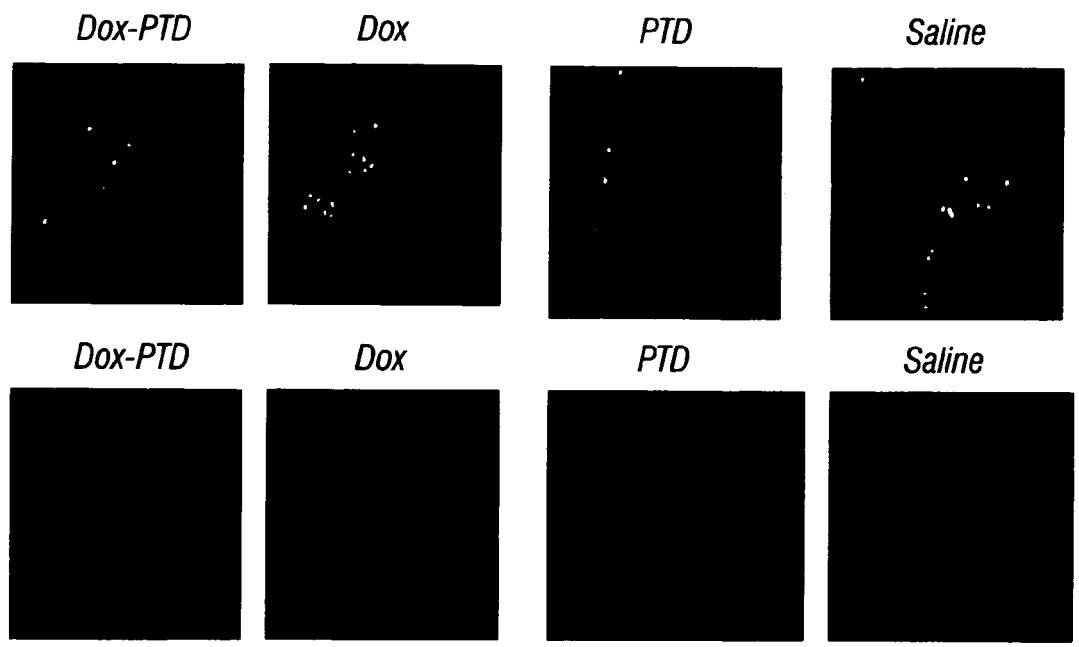
FIG. 11 is a picture of cancer cells after being dosed with (DOX-PTD), doxorubicin, protein-transduction domain, or saline. The dead cells stain red while the live cells stain green.
Figure 12:
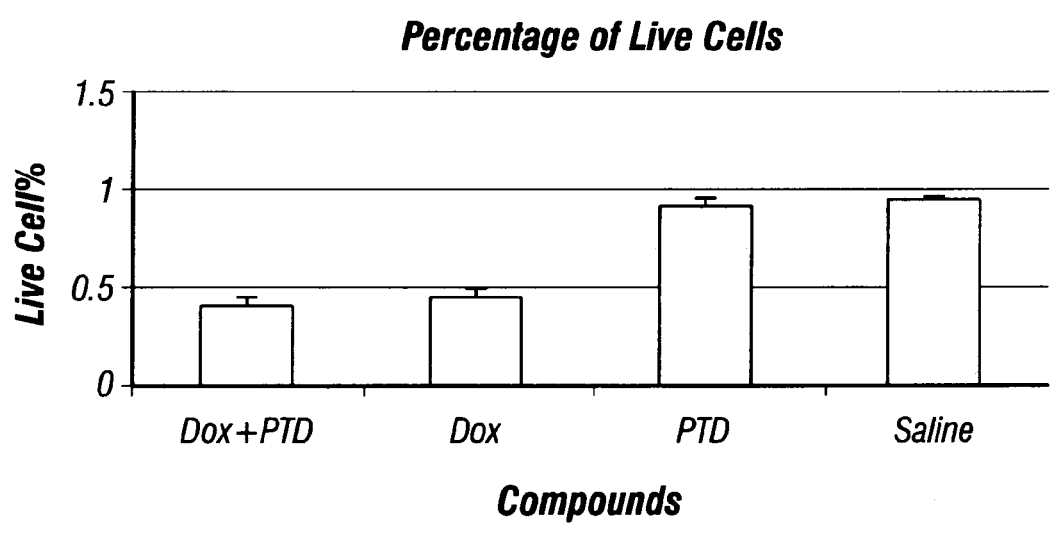
FIG. 12 is a bar graph showing the percentage of live cancer cells after being dosed with (DOX-PTD), doxorubicin, protein-transduction domain, or saline.

FIG. 11 is a picture of cancer cells after being dosed with doxorubicin-protein transduction domain (DOX-PTD), doxorubicin, protein-transduction domain, or saline. FIG. 12 is a bar graph showing the percentage of live cancer cells after being dosed with (DOX-PTD), doxorubicin, protein-transduction domain, or saline. As shown in FIGS. 11 and 12, the number of live cells in the samples with DOX-PTD is less than with Dox alone. Thus, the results indicate that Dox-PTD has greater penetration into the PC-3 cells compared to Dox alone.

Example 11

MTT Studies

Cytotoxicity of PTD carriers were evaluated in mammalian cells using 3-[4,5 dimethylthiazol-2-yl]-2,5-diphenyltetrazolium bromide (MTT). After inducing cytotoxicity (~4 hrs) by routine methods, 10 μl of MTT solution (5.0 mg/ml in PBS, Sigma) was added to each well, and incubated at 37° C. for 3 hrs. The medium was then removed and 200 μl dimethyl sulfoxide (DMSO) was added into each well to dissolve the formazan crystals produced by living cells. The absorbance of the solution was measured at 570 nm. Cell viabilities were calculated using the equation: Viability (%)={$Abs_{570\ (sample)}$/$Abs_{570\ control}$}. A control reaction was run under the same conditions except for the addition of Dox-PTD.

Figure 13:
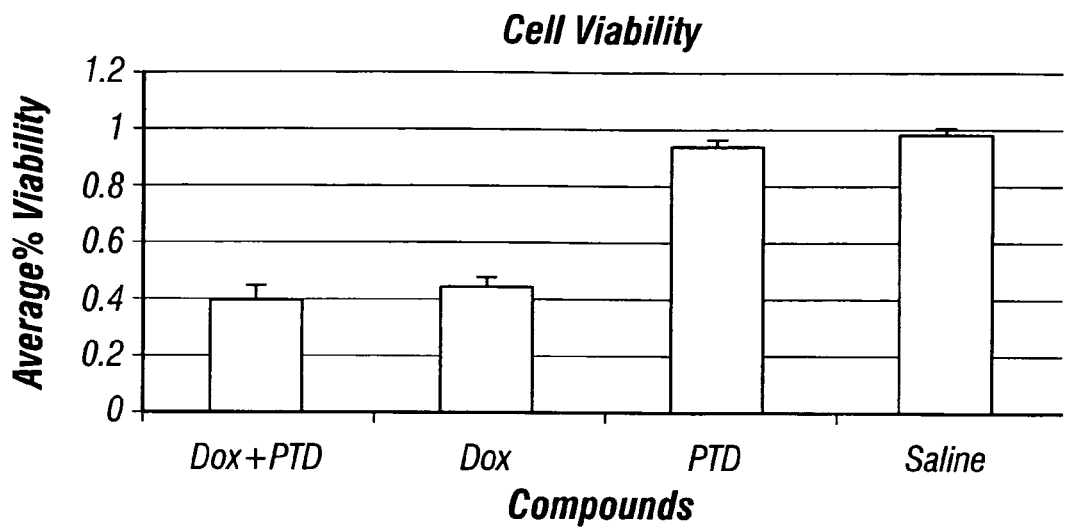
FIG. 13 is a bar graph showing the average viability of mammalian cells after being dosed with (DOX-PTD), doxorubicin, protein-transduction domain, or saline.

FIG. 13 is a bar graph showing the average viability of mammalian cells after being dosed with (DOX-PTD), doxorubicin, protein-transduction domain, or saline. As shown in FIG. 13, the results show that less then 40% of the cells survived after the addition of Dox-PTD. These results demonstrate that the cytotoxicity of Dox-PTD is extremely high.

Example 12

DOX-PTD Anti-tumor Treatment In Vivo Study

1. Establishment Animal Model: Prostate Cancer Animal Model 62 Nude Mice

Male nu/nu athymic mice (6-7 weeks old; 22-25 g; available from Charles River Laboratories) were inoculated subcutaneously on the right flank with $1.1 \times 10^6$ Hela and PC-3 cells to obtain xenografs of human PC-3 prostate cancer.

2. Administration of Doxorubicin, Dox-PTD, PTD and Saline Via Intra-tumor Injection and Intravenously.

Approximately 4 days after inoculation, the four groups of five mice were administered a solution containing saline, doxorubicin, PTD, or DOX-PTD (e.g., $0.103 \times 10^{-4}$ mol) via intra-tumor injection or intravenously. The solution was administered once a week until the total volume administered equaled ~50 μL/mouse. Size measurements of the tumor and the body weight of the mice were taken every other day. A saline solution was used as a control.

TABLE 1

| INTRA-TUMOR INJECTION TREATMENT | | |
|---|---|---|
| Group No. | Drug | Amount |
| A1 | DOX | 0.2 mg/kg ($0.103 \times 10^{-4}$ mol) |
| B1 | DOX-PTD | 0.2 mg/kg ($0.103 \times 10^{-4}$ mol) |
| C1 | Saline | NA |
| F1 | PTD | 0.62 mg/kg ($0.103 \times 10^{-4}$ mol) |

*each group was composed of 5 mice

Figure 14:
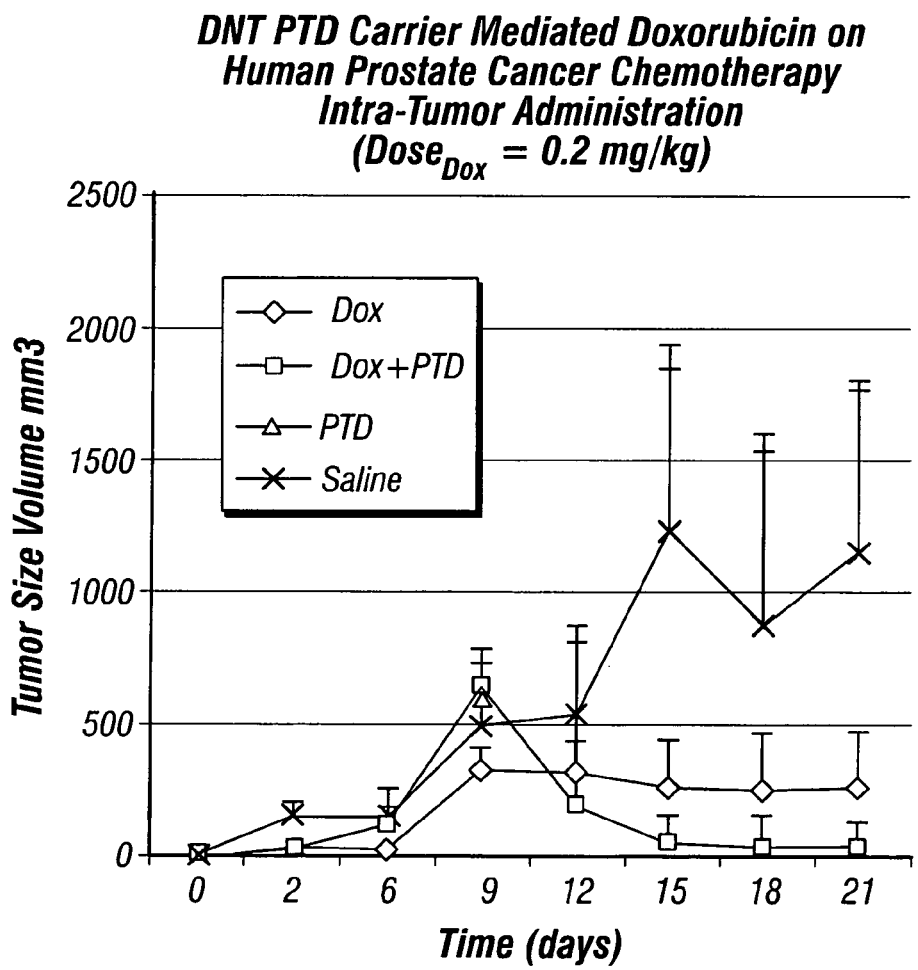
FIGS. 14 and 15 are graphs showing the tumor size of the subjects after intra-tumor administration with (DOX-PTD), doxorubicin, protein-transduction domain, or saline (Dose$_{dox}$=0.2 mg/kg).
Figure 15:
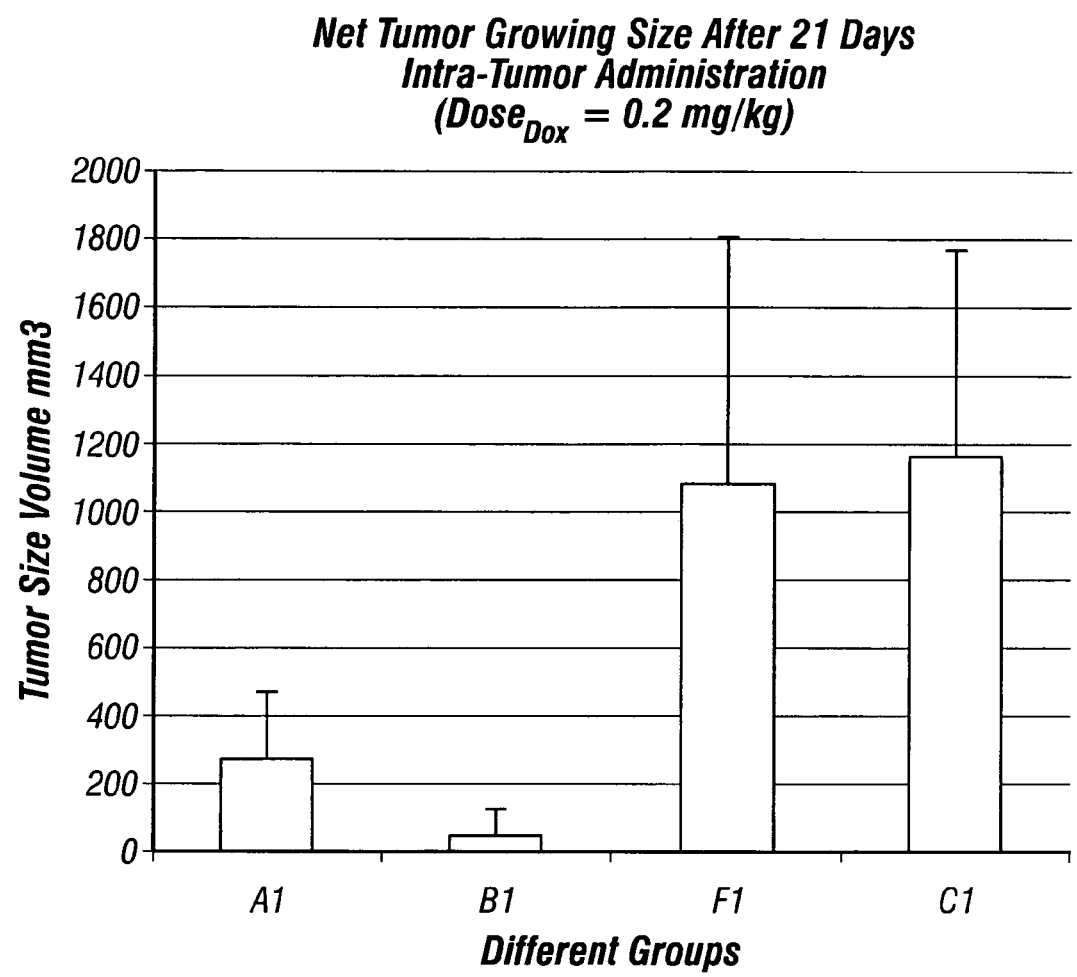

FIGS. 14 and 15 are graphs showing the tumor size of the subjects after intra-tumor administration with (DOX-PTD), doxorubicin, protein-transduction domain, or saline (Dose$_{dox}$=0.2 mg/kg). The results show that a tumor injected with DOX-PTD increased in size less than the tumor injected with Dox alone.

Table 2 is table difference in body weight changes between the groups of mice after being dosed with (DOX-PTD), doxorubicin, protein-transduction domain, or saline. As shown in Table 2, the groups of mice showed no significant difference (No significant statistics, P>0.5) 21 days after dosage.

TABLE 2

DIFFERENCES IN BODY WEIGHT BETWEEN GROUPS
P Volume

| | |
|---|---|
| A1-B1 | 0.475899 |
| A1-C1 | 0.135846 |
| A1-F1 | 0.51353 |
| B1-C1 | 0.196521 |
| B1-F1 | 0.211949 |
| C1-F1 | 0.900519 |

Figure 16:
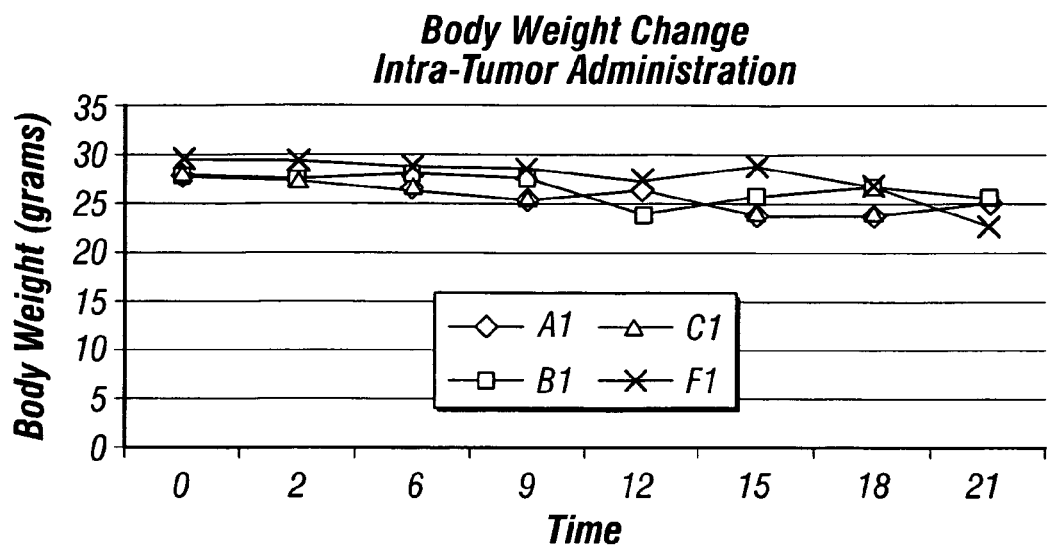
FIG. 16 is a graph showing the body weight changes of the subjects after intra-tumor administration with (DOX-PTD), doxorubicin, protein-transduction domain, or saline.

FIG. 16 is a graph showing the body weight changes of the subjects after intra-tumor administration with (DOX-PTD), doxorubicin, protein-transduction domain, or saline. As shown in FIG. 16, the results show that the body weight of the nude mice after begin inoculated with human prostate cancer cells (PC-3) and (DOX-PTD), doxorubicin, protein-transduction domain, or saline showed no significant difference (No significant statistics, P>0.5) for 21 days after intra-tumor administration.

Example 13

BMPC-Pt, Cisplatin and Carboplatin in B16F0 Cells

1. Cell Work

B16F0 cells (obtained from American Type Culture Collection, ATCC) in RMPI 1640 medium were supplemented with 10% Fetal bovine serum, 2 μM Glutamine, 1 mM non-essential amino acids, 1 mM sodium pyruvate, 100 mg/mL penicillin and 100 μg/mL streptomycin. The cells were harvested from the tissue culture and counted before being resuspended to a concentration of 5×10$^6$/mL.

2. Addition of BMPC-Pt, Cisplatin, and Carboplatin

Using a 6-well plate, approximately 1.5×10$^5$ B16F0 cells were placed in each well with 3 mL media. For every sample, 3 replicates were prepared (3 wells of the 6-well plate). After 24 hrs, a sufficient amount of BMPC-Pt, cisplatin, or carboplatin was added to produce a final concentration of either 25 mM or 50 mM. The cells were allowed to sit at room temperature for either 4 or 24 hours. The media from each well was then aspirated and washed with 2 mL of cold PBS. To ensure that all the cells were adequately rinsed, the 6-well plate was rocked for at least one minute. The cold PBS was then aspirated and the cells were washed again with another 2 mL of cold PBS. This same general procedure was carried out 2 more times. After the washing was completed, 215 μL of 70% nitric acid was added to each well. The cells were then left to sit at room temperature (~25° C.) for approximately 2 hours. The samples were then measured by ICP.

Figure 17:
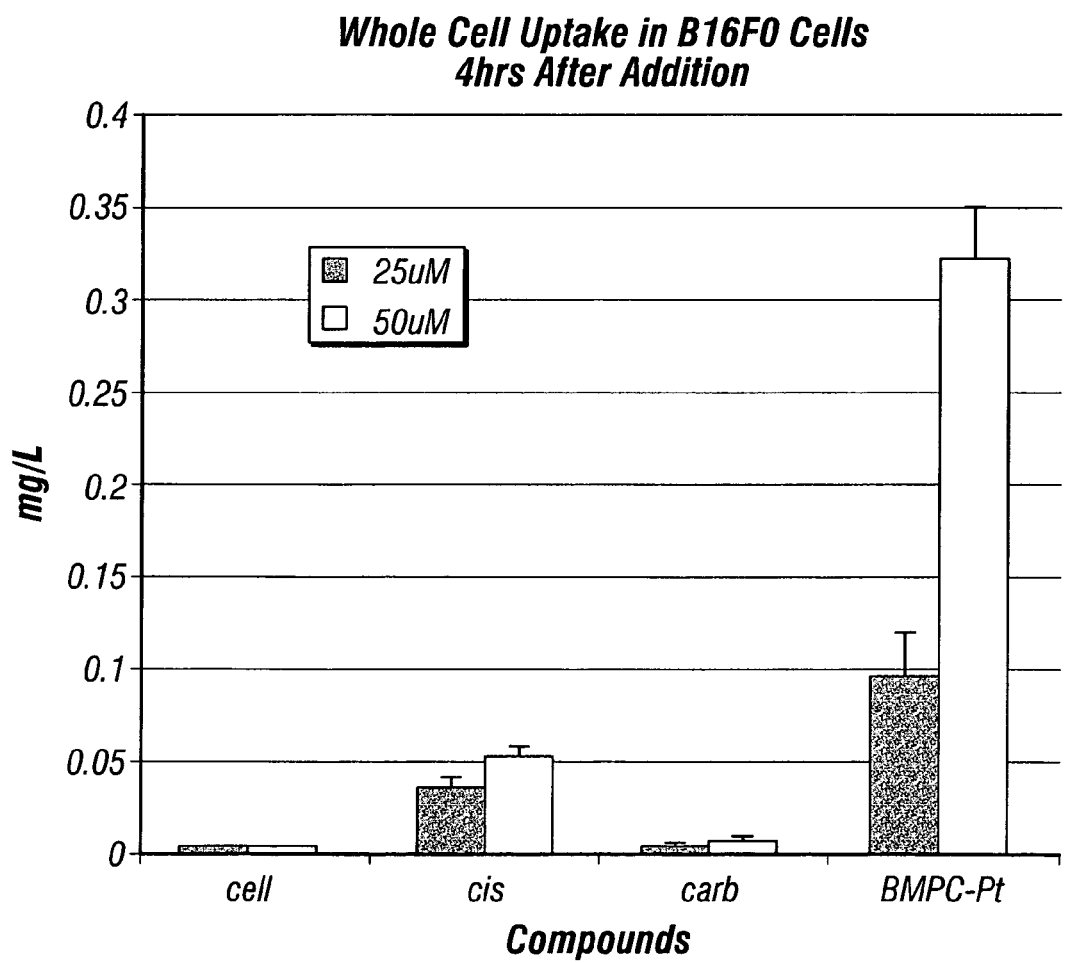
FIG. 17 is a bar graph showing the whole cello uptake in mg/L of BMPC-Pt, Cisplatin, and Carboplatin 4 hours after addition.

FIG. 17 is a bar graph showing the whole cello uptake in mg/L of BMPC-Pt, Cisplatin, and Carboplatin 4 hours after addition. The results show BMPC-Pt uptaken into cells at the concentration of 25 μM is 23 times and 2.7 times greater than Carboplatin and Cisplatin, respectively. The results also show BMPC-Pt uptaken into cells at the concentration of 50 μM is 32 times and 6 times greater than Carboplatin and Cisplatin, respectively.

Figure 18:
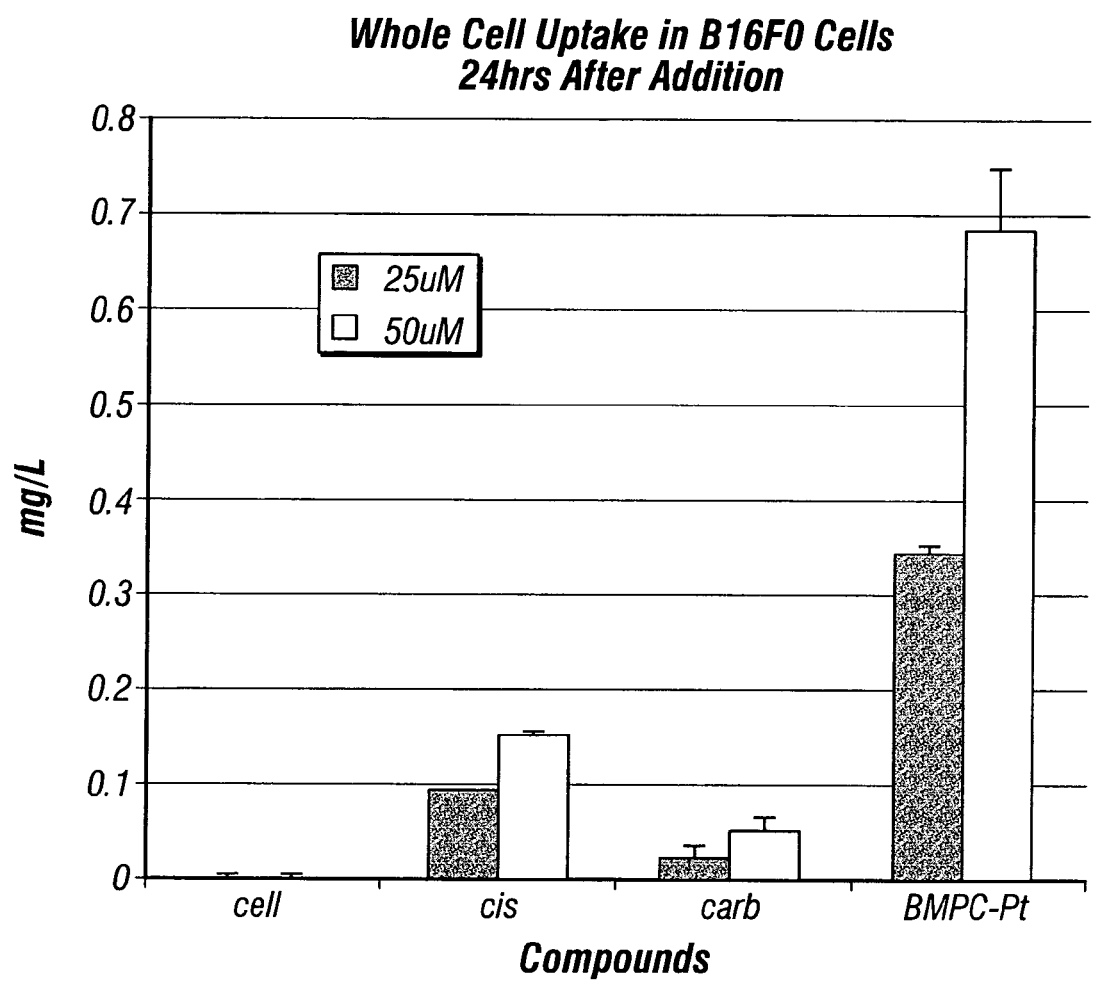
FIG. 18 is a bar graph showing the whole cello uptake in mg/L of BMPC-Pt, Cisplatin, and Carboplatin 24 hours after addition.

FIG. 18 is a bar graph showing the whole cello uptake in mg/L of BMPC-Pt, Cisplatin, and Carboplatin 24 hours after addition. The results show BMPC-Pt uptaken into cells at the concentration of 25 μM is 16 times and 3.8 times greater than Carboplatin and Cisplatin, respectively. The results also show BMPC-Pt uptaken into cells at the concentration of 50 μM is 12.7 times and 4.57 times greater than Carboplatin and Cisplatin, respectively.

Example 14

IC$_{50}$% Study

B16F0 cells (obtained from American Type Culture Collection, ATCC) were split into 96 well plates and incubated at 37° C. under 5% CO$_2$. After 24 hours, BMPC-Pt was added to each well. The fluorescence of each well was measured using two wavelength filters (450 nm and 528 nm) before and several times after BMPC-Pt was added (24, 48, and 72 hours). Using measurements, the fluorescence intensity net increase ratio was calculated and the results are summarized in Table 3 and shown in FIGS. 19 and 20.

TABLE 3

IC 50% STUDY USING B16F0 CELLS

| Time (hours) | BMPC-Pt (μM) | Carboplatin (μM) |
|---|---|---|
| 24 | 127.8 | 109.5 |
| 48 | 51.6 | 36.5 |
| 72 | 22.3 | 24.5 |
| 96 | 12.5 | 4.5 |

Figure 19:
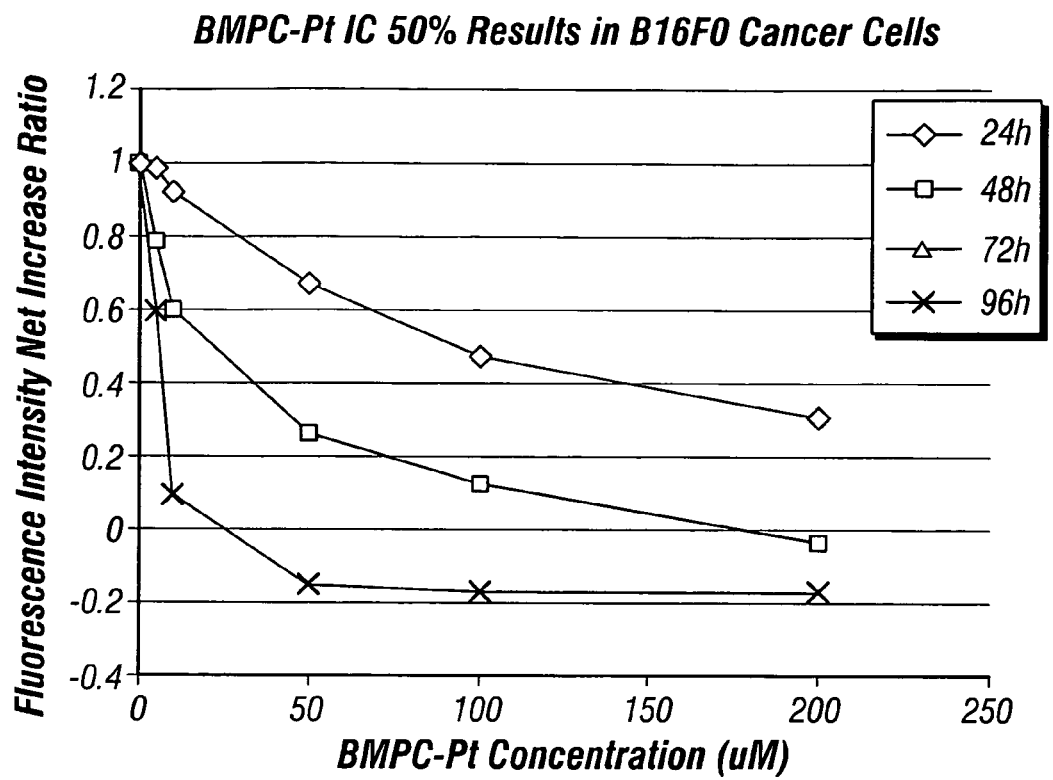
FIGS. 19 and 20 are graphs showing the results of an IC50% study in B16F0 cancer cells with BMPC-Pt and Carboplatin.
Figure 20:
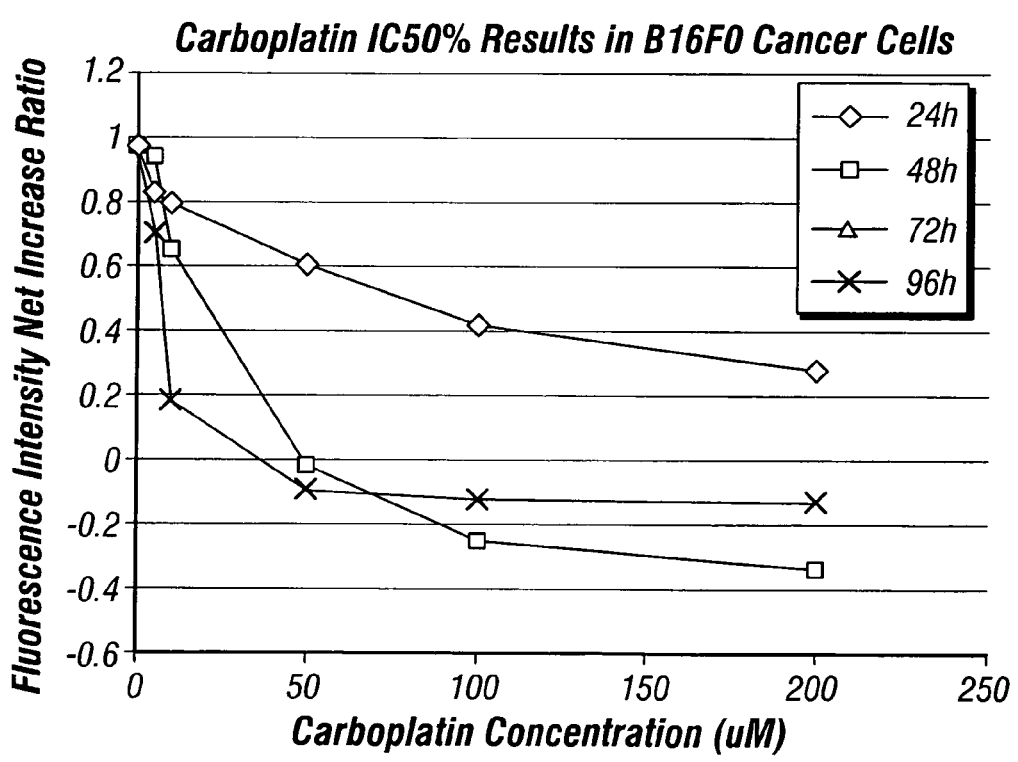

FIGS. 19 and 20 are graphs showing the results of an IC50% study in B16F0 cancer cells using BMPC-Pt and Carboplatin. As shown in FIGS. 19 and 20, BMPC-Pt and carboplatin have similar IC$_{50}$ results over an extended period of time (~96 hours).

Example 15

Tumor Accumulation Study with BMPC-Gd

B16F0 melanoma cells (obtained from American Type Culture Collection, ATCC) in RMPI 1640 medium were supplemented with 10% Fetal bovine serum, 2 μM Glutamine, 1 mM non-essential amino acids, 1 mM sodium pyruvate, 100 mg/mL penicillin and 100 μg/mL streptomycin. The cells were harvested from tissue culture and counted before being resuspended to a concentration of 5×10$^6$/mL. Using a TB syringe, 0.2 mL of the solution containing the suspended cells (approximately 1×10$^6$ cells) was injected subcutaneously into the right hip of male nu/nu athymic mice.

Omniscan-Gd-(DTPA-BMA (0.1 mmolGd/kg) or BMPC-Gd (0.1 mmol Gd/kg) was then injected via a tail vein into the anesthetized mice. Images of the mice were acquired pre-injection and at several times after injection with either Omniscan-Gd or BMPC-Gd. To facilitate imaging a contrasting agent was also injected. Images of mice were obtained on a GE 3T MR scanner with a knee coil pre- and post-contrast using the following imaging parameters: TE: minful, TR: 250 ms, FOV: 8 and 24 slices/slab, and 1.0 mm coronal slice thickness.

Figure 21:
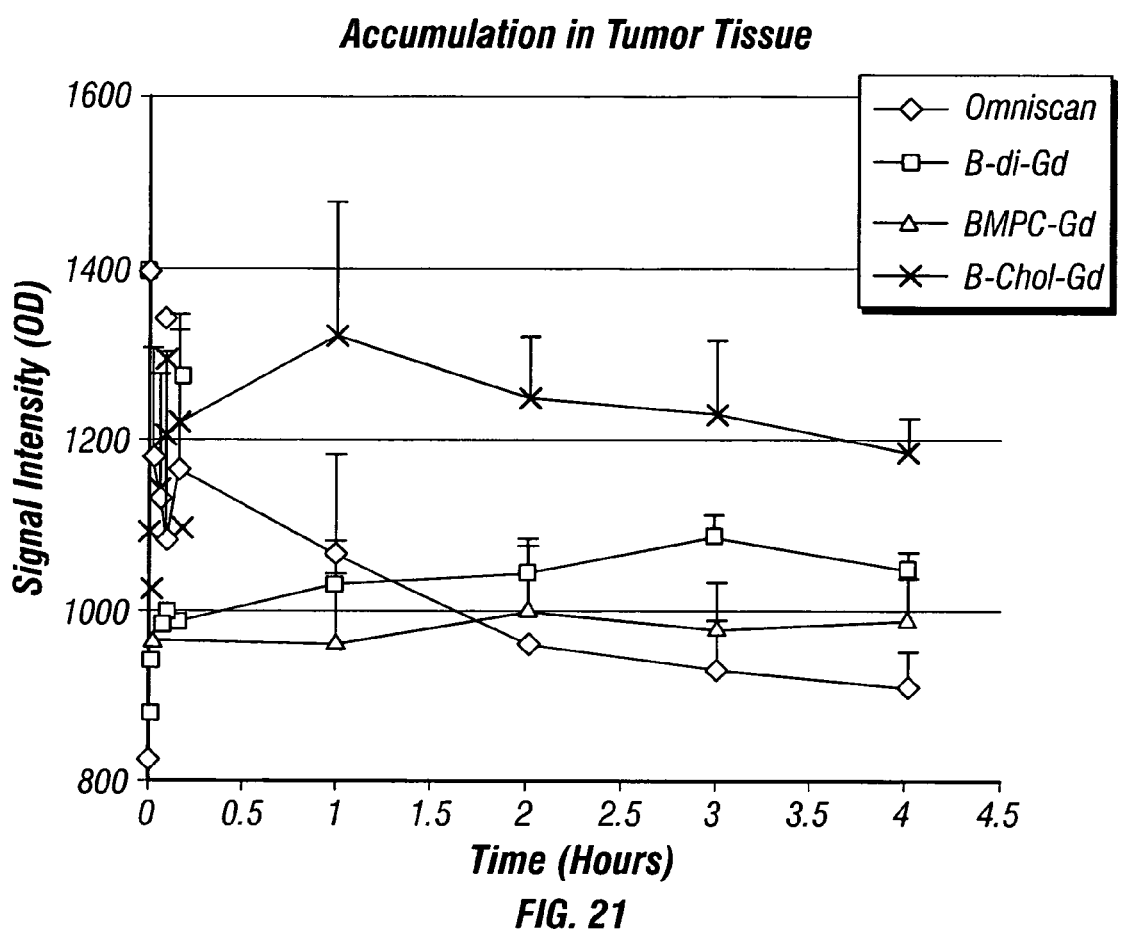
FIG. 21 is graph showing the accumulation of BMPC-Gd and Omniscan in tumor tissue over several hours.

FIG. 21 is graph showing the accumulation of BMPC-Gd and Omniscan in tumor tissue over several hours. As shown in FIG. 21, BMPC-Gd gradually accumulates in the tumor tissue until it reaches its peak concentration 2-3 hours post-injection. The concentration of BMPC-Gd then gradually decreases back to its baseline concentration. These results show BMPC-Gd has both a longer accumulation time and higher accumulation dose compared to Omniscan-Gd.

Although the invention has been described with reference to embodiments and examples, it should be understood that numerous and various modifications can be made without departing from the spirit of the invention. Accordingly, the invention is limited only by the following claims.

What is claimed is:

1. A compound having the following structure:

2. A method for transporting a biologically active moiety across a biological membrane, comprising contacting a biological membrane with the compound of claim 1, or a pharmaceutically acceptable salt thereof.

3. The method of claim 2, wherein the biological membrane is a eukaryotic cell membrane.

4. The method of claim 3, wherein the eukaryotic cell is selected from the group consisting of a mammalian cell, a cancer cell, an insect cell, a plant cell, and a yeast cell.

5. The method of claim 2, wherein said biological membrane is an epithelial layer in a body.

6. The method of claim 5, wherein the epithelial layer is selected from the group consisting of skin, mucosmembrane, and brain blood barriers.

7. The method of claim 2, wherein the biological membrane is a prokaryotic cell membrane.

* * * * *